United States Patent
Gallop et al.

(10) Patent No.: US 7,511,158 B2
(45) Date of Patent: *Mar. 31, 2009

(54) SYNTHESIS OF ACYLOXYALKYL CARBAMATE PRODRUGS AND INTERMEDIATES THEREOF

(75) Inventors: Mark A. Gallop, Santa Clara, CA (US); Xuedong Dai, San Jose, CA (US); Randall A. Scheuerman, Santa Clara, CA (US); Stephen P. Raillard, Mountain View, CA (US); Suresh K. Manthati, Cupertino, CA (US); Fenmei Yao, Mountain View, CA (US); Thu Phan, Fremont, CA (US); Maria Ludwikow, Cupertino, CA (US); Ge Peng, Mountain View, CA (US); Seema Bhat, Santa Clara, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/754,232

(22) Filed: May 25, 2007

(65) Prior Publication Data

US 2007/0244331 A1    Oct. 18, 2007

Related U.S. Application Data

(63) Continuation of application No. 11/026,491, filed on Dec. 30, 2004, now Pat. No. 7,227,028.

(60) Provisional application No. 60/606,637, filed on Aug. 13, 2004, provisional application No. 60/533,649, filed on Dec. 30, 2003.

(51) Int. Cl.
  *C07D 207/46*    (2006.01)
(52) U.S. Cl. .................................... 548/542
(58) Field of Classification Search ................. 548/542
  See application file for complete search history.

(56) References Cited

U.S. PATENT DOCUMENTS

| 4,426,391 A | 1/1984 | Alexander |
| 4,760,057 A | 7/1988 | Alexander |
| 4,916,230 A | 4/1990 | Alexander |
| 5,401,868 A | 3/1995 | Lund |
| 5,733,907 A | 3/1998 | Alexander |
| 2005/0107334 A1 | 5/2005 | Gallop et al. |
| 2005/0222431 A1 | 10/2005 | Gallop |
| 2006/0111325 A1 | 5/2006 | Gallop |
| 2006/0111439 A1 | 5/2006 | Gallop |

FOREIGN PATENT DOCUMENTS

| EP | 0 079 872 A1 | 5/1983 |
| EP | 0416689 | 3/1991 |
| JP | 10148903 | * 6/1998 |
| WO | WO 94/15904 A | 7/1994 |
| WO | WO 01/05813 | 1/2001 |
| WO | WO 2005/019163 | 3/2005 |

OTHER PUBLICATIONS

Mulvihill et al., "Benzaldehyde-derived Chloroformates and their Application towards the Synthesis of Methoxyfenozide-N-[(acyloxy)benzoyloxy)] carbonyl Derivatives," Tetrahedron Lett. 2001, 42, 7751-7754.

Mulvihill, et al., "Synthesis of Insecticidally Active Halofenozide-[(Acyloxy)alkoxy]carbonyl and (Acyloxy)alkyl Derivatives," Synthesis 2002, 1,53-58.

Mutter, et al. "Switch peptides in Statu Nascendi:induction of Conformational Transitions Relevant to Degenerative Diseases," Angewandte Chemie, International Edition, (2004) 43(32) 4172-4178.

Sun, et al., "N-Acylozmethyl Carbamate Linked Prodrugs of Psuedoycins are Novel Anti-fungal agents," Bioorganic & Medicinal Chemistry Letters, 2001, 11(14):1875-1879.

Sun, et al., "Prodrugs of 3-Amindo-Bearing Psuedmycin Analogues: Novel Antifungal Agents," Bioorganic and Chemistry Letters, 2001, 11 1881-1884.

Sun, et al., "Synthesis and Evaluation of Novel Psuedomycin Side-Chain Analogues," Biorganic and Chemistry Letters, 2001, 11, 3055-3059.

* cited by examiner

*Primary Examiner*—Rebecca L Anderson
*Assistant Examiner*—Jason Nolan
(74) *Attorney, Agent, or Firm*—Dorsey & Whitney LLP

(57) ABSTRACT

Methods for synthesis of 1-(acyloxy)-alkyl carbamates, particularly, the synthesis of 1-(acyloxy)-alkyl carbamate prodrugs of primary or secondary amine-containing drugs are described. Also described are methods for synthesis of 1-(acyloxy)-alkyl N-hydroxysuccinimidyl carbonates which are useful intermediates in the synthesis of 1-(acyloxy)-alkyl carbamates are also described.

32 Claims, No Drawings

SYNTHESIS OF ACYLOXYALKYL CARBAMATE PRODRUGS AND INTERMEDIATES THEREOF

This application is a continuation application of U.S. patent application Ser. No. 11/026,491, filed Dec. 30, 2004, which claims priority under 35 U.S.C. § 119 (e) from U.S. Provisional Application Ser. Nos. 60/533,649 and 60/606,637 filed on Dec. 30, 2003 and Aug. 13, 2004, respectively, each of which is incorporated by reference herein in its entirety.

1. FIELD

Methods for synthesis of 1-(acyloxy)-alkyl carbamates are provided. More particularly, the synthesis of 1-(acyloxy)-alkyl carbamate prodrugs of primary or secondary amine-containing drugs is described. Also described are methods for synthesis of 1-(acyloxy)-alkyl N-hydroxysuccinimidyl carbonates.

2. BACKGROUND

One solution to drug delivery and/or bioavailability issues in pharmaceutical development is converting known drugs to prodrugs. Typically, in a prodrug, a polar functional group (e.g., a carboxylic acid, an amino group, a hydroxyl group, etc.) is masked by a promoiety, which is labile under physiological conditions. Accordingly, prodrugs are usually transported through hydrophobic biological barriers such as membranes and typically possess superior physicochemical properties than the parent drug.

The acyloxyalkoxycarbonyl functionality is an example of a promoiety that may be used to modulate the physiochemical properties of pharmaceuticals (Alexander, U.S. Pat. No. 4,916,230; Alexander, U.S. Pat. No. 5,733,907; Alexander et al., U.S. Pat. No. 4,426,391). Typically, 1-(acyloxy)-alkyl derivatives of a pharmaceutical possess superior bioavailability, may be less irritating to topical and/or gastric mucosal membranes and are usually more permeable through such membranes when compared to the parent drug.

However, although 1-(acyloxy)-alkyl carbamate derivatives have been frequently used to mask amine groups in pharmaceuticals, existing synthetic methods for preparing these desirable derivatives are inadequate. Methods disclosed in the art for synthesis of acyloxyalkyl carbamates are typically multi-step routes that utilize unstable intermediates and/or toxic compounds or salts and accordingly are difficult to perform on large scale and in high yield (Alexander, U.S. Pat. No. 4,760,057; Lund, U.S. Pat. No. 5,401,868; Alexander, U.S. Pat. No. 4,760,057; Saari et al., European Patent 0416689B1; Mulvihill et al, *Tetrahedron Lett.* 2001, 7751-7754; Sun et al., *Bioorg. Med. Chem. Lett.* 2001, 11, 1875-1879; Sun et al., *Bioorg. Med. Chem. Lett.* 2001, 11, 3055-3059; Chen et al., International Publication No. WO 01/05813; Mulvihill et al., *Synthesis* 2002, 3, 365-370).

Accordingly, there is a continued need for a new synthesis of 1-(acyloxy)-alkyl carbamates that proceeds rapidly and efficiently, which is amenable to scale-up and proceeds through readily accessible synthetic precursors.

3. SUMMARY

In a first aspect, a method of synthesizing a 1-(acyloxy)-alkyl N-hydroxysuccinimidyl carbonate compound of Formula (I) is provided which comprises

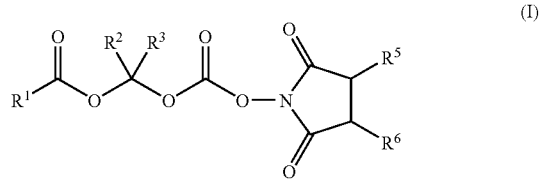

(i) contacting a compound of Formula (IV) and a compound of Formula (V) to provide a compound of Formula (VI);

(ii) contacting the compound of Formula (VI) with a carboxylate compound of Formula (VII) to provide an acyloxyalkyl thiocarbonate compound of Formula (VIII); and (iii) contacting the thiocarbonate compound of Formula (VIII) with an oxidant (IX), in the presence of an N-hydroxysuccinimide compound of Formula (X) to afford the compound of Formula (I);

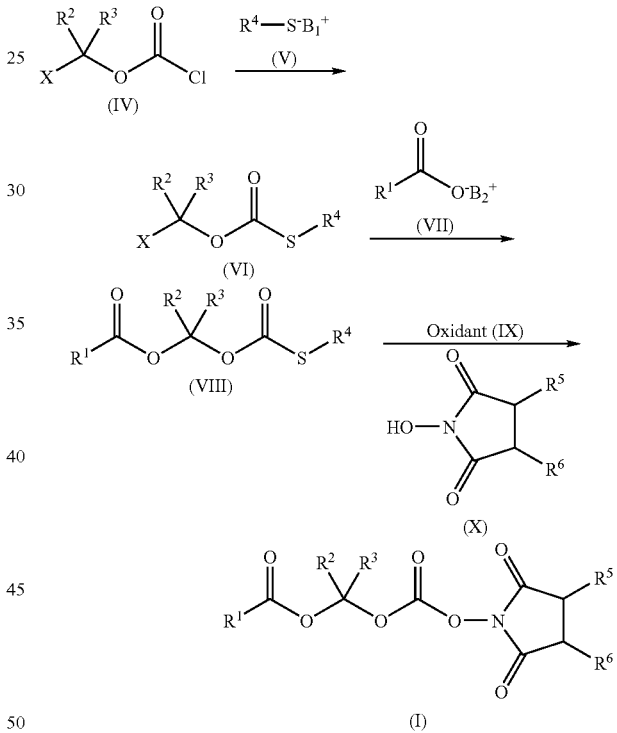

wherein:

X is Cl, Br or I;

$B_1^+$ is an alkali metal cation, a quaternary ammonium cation, or the conjugate acid of an organic base;

$B_2^+$ is a quaternary ammonium cation, the conjugate acid of an organic base, an alkali metal cation, or an alkaline earth metal cation;

$R^1$ is alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl or substituted heteroarylalkyl, or optionally, $R^2$ and $R^3$ together with the atom to which they are bonded form a cycloalkyl, substituted cycloalkyl, cycloheteroalkyl or substituted cycloheteroalkyl ring;

$R^4$ is $C_{1-4}$ alkyl, phenyl, substituted phenyl or $C_{7-9}$ phenylalkyl;

$R^5$ and $R^6$ are independently hydrogen, acylamino, acyloxy, alkoxycarbonylamino, alkoxycarbonyloxy, alkyl, substituted alkyl, alkoxy, substituted alkoxy, aryl, substituted aryl, arylalkyl, carbamoyloxy, dialkylamino, heteroaryl, hydroxy, sulfonamido, or optionally, $R^5$ and $R^6$ together with the atoms to which they are attached form a substituted cycloalkyl, substituted cycloheteroalkyl, or substituted aryl ring.

In a second aspect, a method of synthesizing a 1-(acyloxy)-alkyl carbamate compound of Formula (III) is provided, comprising:

(i) contacting a compound of Formula (IV) and a compound of Formula (V) to provide a compound of Formula (VI);

(ii) contacting the compound of Formula (VI) with a carboxylate compound of Formula (VII) to provide an acyloxyalkyl thiocarbonate compound of Formula (VIII);

(iii) contacting the thiocarbonate compound of Formula (VIII) with an oxidant (IX), in the presence of an N-hydroxysuccinimide compound of Formula (X) to afford the compound of Formula (I); and (iv) contacting the compound of Formula (I) with a primary or secondary amine-containing drug of Formula (II) to afford a compound of Formula (III), or a pharmaceutically acceptable salt, hydrate or solvate thereof;

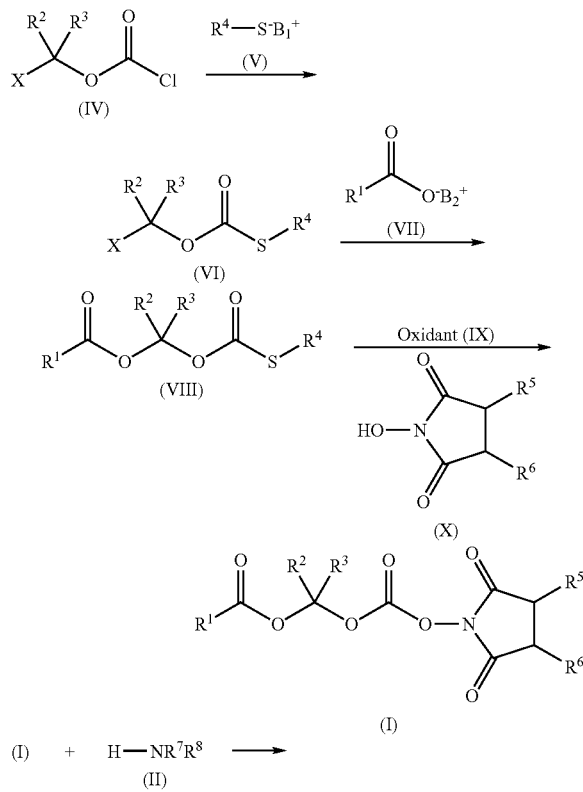

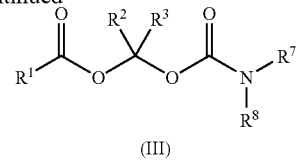

wherein $HNR^7R^8$ is a primary or secondary amine-containing drug and each of X, $B_1^+$, $B_2^+$, and $R^1$ to $R^6$ are as described above.

4. DETAILED DESCRIPTION

4.1 Definitions

"Compounds" refers to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

"1-Acyloxy-Alkyl Carbamate" refers to an N-1-acyloxy-alkoxycarbonyl derivative of a primary or secondary amine-containing drug as encompassed by structural formula (III) herein.

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan- 1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)$R^{30}$, where $R^{30}$ is hydrogen, alkyl, cycloalkyl, cycloheteroalkyl, aryl, arylalkyl, heteroalkyl, heteroaryl or heteroarylalkyl as defined herein. Representative examples include, but are not limited to formyl, acetyl, cyclohexylcarbonyl, cyclohexylmethylcarbonyl, benzoyl, benzylcarbonyl and the like.

"Acylamino" by itself or as part of another substituent refers to a radical —N$R^{31}$C(O)$R^{32}$, where $R^{31}$ and $R^{32}$ are independently hydrogen, alkyl, cycloalkyl, cycloheteroalkyl, aryl, arylalkyl, heteroalkyl, heteroaryl or heteroarylalkyl as defined herein. Representative examples include, but are not limited to formamido, acetamido and benzamido.

"Acyloxy" by itself or as part of another substituent refers to a radical —OC(O)$R^{33}$, where $R^{33}$ is alkyl, cycloalkyl, cycloheteroalkyl, aryl, arylalkyl, heteroalkyl, heteroaryl or heteroarylalkyl as defined herein. Representative examples include, but are not limited to acetoxy, isobutyroyloxy, benzoyloxy, phenylacetoxy and the like.

"Alkali metal" refers to lithium, sodium, potassium, rubidium or cesium.

"Alkaline earth metal" refers to magnesium, calcium, strontium or barium.

"Alkoxy" by itself or as part of another substituent refers to a radical —O$R^{34}$ where $R^{34}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)O$R^{35}$ where $R^{35}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

Alkoxycarbonylamino" by itself or as part of another substituent refers to a radical —N$R^{36}$C(O)O$R^{37}$ where $R^{36}$ represents an alkyl or cycloalkyl group and $R^{37}$ is alkyl, cycloalkyl, cycloheteroalkyl, aryl, arylalkyl, heteroalkyl, heteroaryl, heteroarylalkyl as defined herein. Representative examples include, but are not limited to, methoxycarbonylamino, tert-butoxycarbonylamino and benzyloxycarbonylamino.

Alkoxycarbonyloxy" by itself or as part of another substituent refers to a radical —OC(O)O$R^{38}$ where $R^{38}$ represents an alkyl or cycloalkyl group as defined herein. Representative examples include, but are not limited to, methoxycarbonyloxy, ethoxycarbonyloxy and cyclohexyloxycarbonyloxy.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group is from 6 to 20 carbon atoms. In other embodiments, an aryl group is from 6 to 12 carbon atoms.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In other embodiments, an arylalkyl group is ($C_6$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Carbamoyl" by itself or as part of another substituent refers to the radical —C(O)NR$^{39}$R$^{40}$ where R$^{39}$ and R$^{40}$ are independently hydrogen, alkyl, cycloalkyl or aryl as defined herein.

"Carbamoyloxy" by itself or as part of another substituent refers to the radical —OC(O)NR$^{41}$R$^{42}$ where R$^{41}$ and R$^{42}$ are independently hydrogen, alkyl, cycloalkyl or aryl as defined herein.

"Conjugate acid of an organic base" refers to the protonated form of a primary, secondary or tertiary amine or heteroaromatic nitrogen base. Representative examples include, but are not limited to, triethylammonium, morpholinium and pyridinium.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In some embodiments, the cycloalkyl group is (C$_3$-C$_{10}$) cycloalkyl. In other embodiments, the cycloalkyl group is (C$_3$-C$_7$) cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine, and the like.

"Dialkylamino" by itself or as part of another substituent refers to the radical —NR$^{43}$R$^{44}$ where R$^{43}$ and R$^{44}$ are independently alkyl, cycloalkyl, cycloheteroalkyl, arylalkyl, heteroalkyl or heteroarylalkyl, or optionally R$^{43}$ and R$^{44}$ together with the nitrogen to which they are attached form a cycloheteroalkyl ring.

"GABA analog" refers to a compound, unless specified otherwise, as having the following structure:

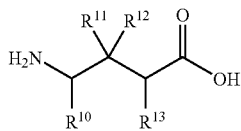

wherein:

R$^{10}$ and R$^{13}$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

R$^{11}$ and R$^{12}$ are independently selected from the group consisting of hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroarylalkyl and substituted heteroarylalkyl, or optionally, R$^{11}$ and R$^{12}$ together with the carbon atom to which they are attached form a cycloalkyl, substituted cycloalkyl, cycloheteroalkyl or substituted cycloheteroalkyl ring.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —NR$^{45}$R$^{46}$, =N—N=, —N=N—, —N=N—NR$^{47}$R$^{48}$, —PR$^{49}$—, —P(O)$_2$—, —POR$^{50}$—, —O—P(O)$_2$—, —SO—, —SO$_2$—, —SnR$^{51}$R$^{52}$— and the like, where R$^{45}$, R$^{46}$, R$^{47}$, R$^{48}$, R$^{49}$, R$^{50}$, R$^{51}$ and R$^{52}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Preferred heteroaryl groups are those derived from thiophene, pyrrole, benzothiophene, benzofuran, indole, pyridine, quinoline, imidazole, oxazole and pyrazine "Heteroarylalkyl" by itself or as part of another substituent refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In some embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In other embodiments, the heteroarylalkyl group is a 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Parent Aromatic Ring System" by itself or as part of another substituent refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" by itself or as part of another substituent refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Prodrug" refers to a derivative of a drug molecule that requires a transformation within the body to release the active drug. Prodrugs are frequently, although not necessarily, pharmacologically inactive until converted to the parent drug. A hydroxyl containing drug may be converted to, for example, to a sulfonate, ester or carbonate prodrug, which may be hydrolyzed in vivo to provide the hydroxyl compound. An amino containing drug may be converted, for example, to a carbamate, amide, enamine, imine, N-phosphonyl, N-phosphoryl or N-sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which have functional groups different than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al, "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substantially one diastereomer" refers to a compound containing 2 or more stereogenic centers such that the diastereomeric excess (d.e.) of the compound is at least 90%, preferably greater than 95%, more preferably greater than 98%, and most preferably greater than 99%.

"Substituted" refers to a group in which one or more hydrogen atoms are independently replaced with the same or different substituent(s). In some embodiments, substituents include -M, —$R^{60}$, —$O^-$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2O^-$, —$S(O)_2OH$, —$S(O)_2R^{60}$, —$OS(O_2)O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$ —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$, where M is independently a halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In other embodiments, substituents include -M, —$R^{60}$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O_2)O^-$; —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$. In still other embodiments, substituents include -M, —R , =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$. In still other embodiements, substituents include -M, —$R^{60}$, =O, —$OR^{60}$, —$SR^{60}$, —$NR^{60}R^{61}$, —$CF_3$, —CN, —$NO_2$—$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above.

"Sulfonamido" by itself or as part of another substituent refers to a radical —$NR^{53}S(O)_2R^{54}$, where $R^{53}$ is alkyl, substituted alkyl, cycloalkyl, cycloheteroalkyl, aryl, substituted aryl, arylalkyl, heteroalkyl, heteroaryl or heteroarylalkyl and $R^{54}$ is hydrogen, alkyl, cycloalkyl, cycloheteroalkyl, aryl, arylalkyl, heteroalkyl, heteroaryl or heteroarylalkyl as defined herein. Representative examples include, but are not limited to methanesulfonamido, benzenesulfonamido and p-toluenesulfonamido.

Reference will now be made in detail to embodiments of the invention. While the invention will be described in conjunction with these embodiments, it will be understood that it is not intended to limit the invention to those embodiments. To the contrary, it is intended to cover alternatives, modifications, and equivalents as may be included within the spirit and scope of the invention as defined by the appended claims.

4.2 Method of Synthesis of 1-(Acyloxy)-Alkyl N-Hydroxysuccinimidyl Carbonates

In a first aspect, a method of synthesizing a 1-(acyloxy)-alkyl N-hydroxysuccinimidyl carbonate compound of Formula (I) is provided,

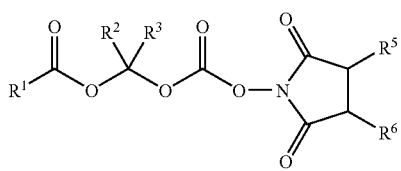

which comprises:

(i) contacting a compound of Formula (IV) and a compound of Formula (V) to provide a compound of Formula (VI);

(ii) contacting the compound of Formula (VI) with a carboxylate compound of Formula (VII) to provide an acyloxyalkyl thiocarbonate compound of Formula (VIII); and (iii) contacting the thiocarbonate compound of Formula (VIII) with an oxidant (IX), in the presence of an N-hydroxysuccinimide compound of Formula (X) to afford the compound of Formula (I);

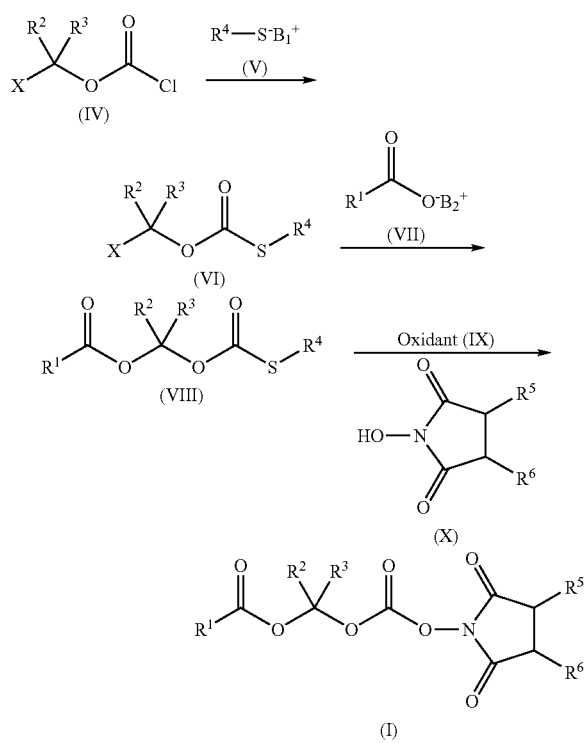

wherein:

X is Cl, Br or I;

$B_1^+$ is an alkali metal cation, a quaternary ammonium cation, or the conjugate acid of an organic base;

$B_2^+$ is a quaternary ammonium cation, the conjugate acid of an organic base, an alkali metal cation, or an alkaline earth metal cation;

$R^1$ is alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl or substituted heteroarylalkyl, or optionally, $R^2$ and $R^3$ together with the atom to which they are bonded form a cycloalkyl, substituted cycloalkyl, cycloheteroalkyl or substituted cycloheteroalkyl ring;

$R^4$ is $C_{1-4}$ alkyl, phenyl, substituted phenyl or $C_{7-9}$ phenylalkyl;

$R^5$ and $R^6$ are independently hydrogen, acylamino, acyloxy, alkoxycarbonylamino, alkoxycarbonyloxy, alkyl, substituted alkyl, alkoxy, substituted alkoxy, aryl, substituted aryl, arylalkyl, carbamoyloxy, dialkylamino, heteroaryl, hydroxy, sulfonamido, or optionally, $R^5$ and $R^6$ together with the atoms to which they are attached form a substituted cycloalkyl, substituted cycloheteroalkyl, or substituted aryl ring.

In some embodiments, X is Cl.

In some other embodiments, $R^1$ is selected from the group consisting of $C_{1-6}$ alkyl, substituted $C_{1-6}$ alkyl, $C_{3-6}$ cycloalkyl, phenyl, substituted phenyl and $C_{7-9}$ phenylalkyl. In other embodiments, $R^1$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl or cyclohexyl. In still other embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl or cyclohexyl.

In still other embodiments, $R^2$ and $R^3$ are independently selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl and substituted heteroarylalkyl. In still other embodiments, $R^2$ and $R^3$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl and $C_{7-9}$ phenylalkyl. In still other embodiments, $R^2$ and $R^3$ are independently selected from the group consisting of hydrogen, methyl, ethyl, propyl, isopropyl, butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl and phenethyl. In still another embodiment, $R^2$ is hydrogen, methyl, ethyl, n-propyl, isopropyl, n-butyl, isobutyl, sec-butyl, phenyl or cyclohexyl and $R^3$ is hydrogen. In still other embodiments, $R^2$ is methyl, methoxycarbonyl, ethoxycarbonyl, isopropoxycarbonyl or cyclohexyloxycarbonyl and $R^3$ is methyl. In still other embodiments, $R^2$ and $R^3$ together with the carbon atom to which they are attached form a cycloalkyl, substituted cycloalkyl, cycloheteroalkyl or substituted cycloheteroalkyl ring. In still other embodiments, $R^2$ and $R^3$ together with the carbon atom to which they are attached form a cyclobutyl, cyclopentyl or cyclohexyl ring.

In still other embodiments, $R^4$ is $C_{1-4}$ alkyl, phenyl, substituted phenyl or $C_{7-9}$ phenylalkyl. In still other embodiments, $R^4$ is methyl, ethyl, propyl, isopropyl, butyl, isobutyl, sec-butyl, tert-butyl, phenyl, 4-methoxyphenyl, 4-methylphenyl or benzyl.

In still other embodiments, $R^5$ and $R^6$ are independently hydrogen, acylamino, acyloxy, alkoxycarbonylamino, alkoxycarbonyloxy, alkoxy, substituted alkoxy, carbamoyloxy, dialkylamino, hydroxy, sulfonamido or optionally, $R^5$ and $R^6$ together with the atoms to which they are attached form a substituted cycloalkyl, substituted cycloheteroalkyl or substituted aryl ring. In still other embodiments, $R^5$ and $R^6$ are both hydrogen. In still other embodiments, $R^5$ and $R^6$ are each acyloxy, alkoxycarbonyloxy, alkoxy, carbamoyloxy or hydroxy. In still other embodiments, $R^5$ and $R^6$ are both acetoxy, isobutyroyloxy, pivaloyloxy, benzoyloxy, $C_{1-4}$ alkyl-substituted benzoyloxy, methoxy or benzyloxy. In still other embodiments, $R^5$ and $R^6$ are both benzoyloxy. In still other embodiments, $R^5$ is acylamino, acyloxy, alkoxycarbonylamino, alkoxycarbonyloxy, alkoxy, substituted alkoxy, carbamoyloxy, dialkylamino, hydroxy, or sulfonamido and $R^6$ is hydrogen. In still other embodiments, $R^5$ and $R^6$ together with the atoms to which they are attached form a 1,2-disubstituted cyclohexyl or 1,2-disubstituted phenyl ring.

In still other embodiments, $R^1$ is selected from the group consisting of $C_{1-6}$ alkyl, substituted $C_{1-6}$ alkyl, $C_{3-6}$ cycloalkyl, phenyl, substituted phenyl and $C_{7-9}$ phenylalkyl, $R^2$ and $R^3$ are independently selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl and substituted heteroarylalkyl, $R^4$ is $C_{1-4}$ alkyl, phenyl, substituted phenyl or $C_{7-9}$ phenylalkyl and $R^5$ and $R^6$ are independently hydrogen, acylamino, acyloxy, alkoxycarbonylamino, alkoxycarbonyloxy, alkoxy, substituted alkoxy, carbamoyloxy, dialkylamino, hydroxy, sulfonamido or optionally, $R^5$ and $R^6$ together with the atoms to which they are attached form a substituted cycloalkyl, substituted cycloheteroalkyl or substituted aryl ring. In still other embodiments, $R^1$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl or cyclohexyl, $R^2$ and $R^3$ are independently selected from the group consisting of hydrogen, methyl, ethyl, propyl, isopropyl, butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl and phenethyl, $R^4$ is methyl, ethyl, propyl, isopropyl, butyl, isobutyl, sec-butyl, tert-butyl, phenyl, 4-methoxyphenyl, 4-methylphenyl or benzyl and $R^5$ and $R^6$ are each acyloxy, alkoxycarbonyloxy, alkoxy, carbamoyloxy or hydroxy. In still other embodiments, $R^1$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl or cyclohexyl, $R^2$ and $R^3$ are independently selected from the group consisting of hydrogen, methyl, ethyl, propyl, isopropyl, butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl and phenethyl, $R^4$ is methyl, ethyl, propyl, isopropyl, butyl, isobutyl, sec-butyl, tert-butyl, phenyl, 4-methoxyphenyl, 4-methylphenyl or benzyl and $R^5$ and $R^6$ are both acetoxy, isobutyroyloxy, pivaloyloxy, benzoyloxy, $C_{1-4}$ alkyl-substituted benzoyloxy, methoxy or benzyloxy. In still other embodiments, $R^1$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl or cyclohexyl, $R^2$ and $R^3$ are independently selected from the group consisting of hydrogen, methyl, ethyl, propyl, isopropyl, butyl, isobutyl, sec-butyl, tert-butyl, cyclopentyl, cyclohexyl, methoxycarbonyl, ethoxycarbonyl, isopropoxycarbonyl, cyclohexyloxycarbon-yl, phenyl, benzyl and phenethyl, $R^4$ is methyl, ethyl, propyl, isopropyl, butyl, isobutyl, sec-butyl, tert-butyl, phenyl, 4-methoxyphenyl, 4-methylphenyl or benzyl, $R^5$ is acylamino, acyloxy, alkoxycarbonylamino, alkoxycarbonyloxy, alkoxy, substituted alkoxy, carbamoyloxy, dialkylamino, hydroxy, or sulfonamido and $R^6$ is hydrogen. In still other embodiments, $R^1$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl or cyclohexyl, $R^2$ and $R^3$ are independently selected from the group consisting of hydrogen, methyl, ethyl, propyl, isopropyl, butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl and phenethyl, $R^4$ is methyl, ethyl, propyl, isopropyl, butyl, isobutyl, sec-butyl, tert-butyl, phenyl, 4-methoxyphenyl, 4-methylphenyl or benzyl and $R^5$ and $R^6$ together with the atoms to which they are attached form a 1,2-disubstituted cyclohexyl or 1,2-disubstituted phenyl ring.

In some embodiments, $R^1$ is isopropyl, $R^2$ is methyl, $R^3$ is hydrogen, $R^4$ is methyl, ethyl or tert-butyl, and $R^5$ and $R^6$ are each hydrogen. In other embodiments, $R^1$ is isopropyl, $R^2$ is isopropyl, $R^3$ is hydrogen, $R^4$ is methyl, ethyl or tert-butyl, and $R^5$ and $R^6$ are each benzoyloxy. In still other embodiments, $R^1$ is isopropyl, $R^2$ is isopropyl, $R^3$ is hydrogen, $R^4$ is methyl, ethyl or tert-butyl, and $R^5$ and $R^6$ are each isobutyroyloxy. In still other embodiments, $R^1$ is isopropyl, $R^2$ is isopropyl, $R^3$ is hydrogen, $R^4$ is methyl, ethyl or tert-butyl and $R^5$ and $R^6$ are each pivaloyloxy. In still other embodiments, $R^1$ is isopropyl, $R^2$ is isopropyl, $R^3$ is hydrogen, $R^4$ is methyl, ethyl or tert-butyl, and $R^5$ and $R^6$ are each $C_{1-4}$ alkyl-substituted benzoyloxy.

In some embodiments, $R^2$ and $R^3$ in the compound of Formula (I) are different, such that the carbon atom to which $R^2$ and $R^3$ are attached is a stereogenic center. In other embodiments, the compound of Formula (X) is chiral and non-racemic.

In some embodiments, $R^5$ and $R^6$ in the compound of Formula (X) are each benzoyloxy, the stereochemistry at the carbon to which $R^5$ is attached is of the R-configuration and the stereochemistry at the carbon to which $R^6$ is attached is of the R-configuration. In other embodiments, $R^5$ and $R^6$ in the compound of Formula (X) are each benzoyloxy, the stereochemistry at the carbon to which $R^5$ is attached is of the S-configuration, and the stereochemistry at the carbon to which $R^6$ is attached is of the S-configuration.

In some embodiments, $R^5$ and $R^6$ in the compound of Formula (X) are each isobutyroyloxy, the stereochemistry at the carbon to which $R^5$ is attached is of the R-configuration and the stereochemistry at the carbon to which $R^6$ is attached is of the R-configuration. In other embodiments, $R^5$ and $R^6$ in the compound of Formula (X) are each isobutyroyloxy, the stereochemistry at the carbon to which $R^5$ is attached is of the S-configuration, and the stereochemistry at the carbon to which $R^6$ is attached is of the S-configuration.

In some embodiments, $R^5$ and $R^6$ in the compound of Formula (X) are each pivaloyloxy, the stereochemistry at the carbon to which $R^5$ is attached is of the R-configuration and the stereochemistry at the carbon to which $R^6$ is attached is of the R-configuration. In other embodiments of the method for synthesizing a compound of Formula (I), $R^5$ and $R^6$ in the compound of Formula (X) are each pivaloyloxy, the stereochemistry at the carbon to which $R^5$ is attached is of the S-configuration, and the stereochemistry at the carbon to which $R^6$ is attached is of the S-configuration.

In some embodiments, $R^5$ and $R^6$ in the compound of Formula (X) are each $C_{1-4}$ alkyl-substituted benzoyloxy, the stereochemistry at the carbon to which $R^5$ is attached is of the R-configuration, and the stereochemistry at the carbon to which $R^6$ is attached is of the R-configuration. In other embodiments, $R^5$ and $R^6$ in the compound of Formula (X) are each $C_{1-4}$ alkyl-substituted benzoyloxy, the stereochemistry at the carbon to which $R^5$ is attached is of the S-configuration, and the stereochemistry at the carbon to which $R^6$ is attached is of the S-configuration.

In some embodiments, $R^2$ and $R^3$ in the compound of Formula (I) are different and the compound comprises substantially one diastereomer.

In some embodiments, the compound of Formula (I) is substantially one diastereomer, wherein $R^1$ is isopropyl, $R^2$ is isopropyl, $R^3$ is hydrogen, $R^4$ is methyl, ethyl or tert-butyl, $R^5$ and $R^6$ are each benzoyloxy, the stereochemistry at the carbon to which $R^2$ and $R^3$ are attached is of the S-configuration, the stereochemistry at the carbon to which $R^5$ is attached is of the R-configuration, and the stereochemistry at the carbon to which $R^6$ is attached is of the R-configuration. In other embodiments, the compound of Formula (I) is substantially one diastereomer, wherein $R^1$ is isopropyl, $R^2$ is isopropyl, $R^3$ is hydrogen, $R^4$ is methyl, ethyl or tert-butyl, $R^5$ and $R^6$ are each benzoyloxy, the stereochemistry at the carbon to which $R^2$ and $R^3$ are attached is of the R-configuration, the stereochemistry at the carbon to which $R^5$ is attached is of the S-configuration, and the stereochemistry at the carbon to which $R^6$ is attached is of the S-configuration.

In some embodiments, the compound of Formula (I) is substantially one diastereomer, wherein $R^1$ is isopropyl, $R^2$ is isopropyl, $R^3$ is hydrogen, $R^4$ is methyl, ethyl or tert-butyl, $R^5$ and $R^6$ are each isobutyroyloxy, the stereochemistry at the carbon to which $R^2$ and $R^3$ are attached is of the S-configuration, the stereochemistry at the carbon to which $R^5$ is attached is of the S-configuration, and the stereochemistry at the carbon to which $R^6$ is attached is of the S-configuration. In other embodiments, the compound of Formula (I) is substantially one diastereomer, wherein $R^1$ is isopropyl, $R^2$ is isopropyl, $R^3$ is hydrogen, $R^4$ is methyl, ethyl or tert-butyl, $R^5$ and $R^6$ are each isobutyroyloxy, the stereochemistry at the carbon to which $R^2$ and $R^3$ are attached is of the R-configuration, the stereochemistry at the carbon to which $R^5$ is attached is of the R-configuration, and the stereochemistry at the carbon to which $R^6$ is attached is of the R-configuration.

In some embodiments, $B_1^+$ of Formula (V) is an alkali metal cation. In other embodiments, $B_1^+$ is a lithium, sodium or potassium ion. In still other embodiments, $B_1^+$ is a sodium ion.

In some embodiments, $B_1^+$ is a quaternary ammonium cation. In other embodiments, $B_1^+$ is a tetramethylammonium, tetraethylammonium or tetrabutylammonium cation. In still other embodiments, $B_1^+$ is the conjugate acid of an organic base. In still other embodiments, $B_1^+$ is the conjugate acid of triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, or 1,5-diazabicyclo[4.3.0]undec-7-ene, more preferably, $B_1^+$ is a triethylammonium, diisopropylethylammonium, N-methylmorpholinium or pyridinium cation.

In some embodiments, a solvent is used in the first step of the above method. Solvents useful in step (i) include, but are not limited to, dichloromethane, dichloroethane, chloroform, toluene, tetrahydrofuran, dioxane, dimethylformamide, dimethylacetamide, N-methylpyrrolidinone, dimethyl sulfoxide, pyridine, ethyl acetate, acetonitrile, methyl tert-butyl ether, water or combinations thereof. In some embodiments, the solvent is dichloromethane, toluene, tetrahydrofuran, pyridine, methyl tert-butyl ether, water, or combinations thereof. In other embodiments, the solvent is dichloromethane, water or a combination thereof. In still other embodiments, the solvent is a biphasic mixture of dichloromethane and water. In still other embodiments, the solvent is a biphasic mixture of dichloromethane and water containing from about 0.001 equivalents to about 0.1 equivalents of a phase transfer catalyst. In still other embodiments, the phase transfer catalyst is a tetraalkylammonium salt, more preferably, a tetrabutylammonium salt.

In some embodiments, step (i) is carried out at a temperature between about −20° C. and about 25° C. In other embodiments, step (i) is carried out at a temperature between about 0° C. and about 25° C.

In some embodiments, $B_2^+$ in the carboxylate salt of Formula (VII) is a quaternary ammonium cation. In other embodiments, $B_2^+$ is a tetramethylammonium, tetraethylammonium or tetrabutylammonium cation.

In some embodiments, $B_2^+$ is the conjugate acid of an organic base. In other embodiments, $B_2^+$ is the conjugate acid of triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene or 1,5-diazabicyclo[4.3.0]undec-7-ene. In still other embodiments, $B_2^+$ is a triethylammonium, diisopropylethylammonium, N-methylmorpholinium or pyridinium cation.

In some embodiments, $B_2^+$ is an alkali metal cation. In other embodiments, $B_2^+$ is a lithium, sodium or potassium ion.

In some embodiments, a solvent is used in step (ii) of the above method. Solvents useful in the second step include, but are not limited to, tetrahydrofuran, dioxane, dichloromethane, dichloroethane, chloroform, toluene, dimethylformamide, dimethylacetamide, N-methylpyrrolidinone, dimethyl sulfoxide, pyridine, ethyl acetate, acetonitrile, methyl tert-butyl ether, methanol, ethanol, isopropanol, tert-butanol, water, or combinations thereof. In some embodiments, the solvent is tetrahydrofuran, dioxane, dichloromethane, toluene, pyridine, methyl tert-butyl ether, methanol, ethanol, isopropanol, water or combinations thereof. In other embodiments, the solvent is tetrahydrofuran. In still other embodiments, the solvent used in step (ii) of the above method is the conjugate acid of the compound of Formula (VII).

In some embodiments, step (ii) is carried out a temperature between about −20° C. and about 100° C. In other embodiments, step (ii) is carried out a temperature between about 0° C. and about 25° C. In still other embodiments, step (ii) is carried out a temperature between about 25° C. and about 80° C.

In some embodiments, oxidant (IX) is a peroxy acid, a peroxide, ozone or oxygen. In other embodiments, oxidant (IX) is a stoichiometric or catalytic amount of a transition metal compound. In still other embodiments, oxidant (IX) is a peroxy acid, a peroxide, ozone or oxygen with a catalytic amount of a transition metal compound.

Suitable peroxy acids include, but are not limited to, peroxyacetic acid, m-chloroperoxybenzoic acid, peroxytrifluoroacetic acid, peroxydifluoroacetic acid, peroxyfluoroacetic acid, peroxytrichloroacetic acid, peroxydichloroacetic acid, peroxychloroacetic acid, peroxytribromoacetic acid, peroxydibromoacetic acid, peroxybromoacetic acid, peroxychlorodifluoroacetic acid, peroxypentafluoropropionic acid, peroxybenzoic acid, p-fluoroperoxybenzoic acid, pentafluoroperoxybenzoic acid, p-trifluoroperoxybenzoic acid, o-nitroperoxybenzoic acid, m-nitroperoxybenzoic acid, p-nitroperoxybenzoic acid, 3,5-dinitroperoxybenzoic acid, monoperoxysuccinic acid, monoperoxymaleic acid, monoperoxy-o-phthalic acid, peroxytrifluromethanesulfonic acid, peroxymethanesulfonic acid, p-tolueneperoxysulfonic acid, peroxybenzene sulfonic acid and salts thereof. In some embodiments, the peroxy acid is peroxyacetic acid, m-chloroperoxybenzoic acid, monoperoxy-o-phthalic acid, monoperoxymaleic acid, peroxytrifluoroacetic acid or salts thereof. In other embodiments, the the peroxy acid is peroxyacetic acid, m-chloroperoxybenzoic acid, magnesium monoperoxy-o-phthalate or salts thereof.

In some embodiments, the peroxy acid is synthesized by contacting urea-hydrogen peroxide complex with an acid anhydride. In other embodiments, the peroxy acid is synthesized by contacting urea-hydrogen peroxide complex with maleic anhydride.

In some embodiments, the molar ratio of oxidant (IX), to thiocarbonate, (VIII), is between about 10:1 and about 1:1. In other embodiments, the molar ratio of oxidant (IX), to thiocarbonate, (VIII), the molar ratio of oxidant (IX), to thiocarbonate, (VIII), is between about 3:1 and about 1:1. In still other embodiments, the molar ratio of acid anhydride to the urea-hydrogen peroxide complex is between about 6:1 and about 1:1.

In some embodiments, a solvent is used in the third step of the above method. Solvents useful in step (iii) include, but are not limited to, acetic acid, dichloromethane, dichloroethane, chloroform, ethyl acetate, toluene, chlorobenzene, xylene, acetonitrile, methyl tert-butyl ether, cyclohexane or combinations thereof. In some embodiments, the solvent is acetic acid, dichloromethane, dichloroethane or combinations thereof.

In some embodiments, step (iii) is carried out a temperature between about −20° C. and about 80° C. In other embodiments, step (iii) is carried out a temperature between about −20° C. and about 25° C. In still other embodiments, step (iii) is carried out a temperature between about 25° C. and about 60° C.

In some embodiments of step (iii), the reaction is performed in the presence of an inorganic base. In some embodiments, the inorganic base is an alkali metal bicarbonate or alkali metal carbonate salt. In other embodiments, the inorganic base is sodium bicarbonate.

In some embodiments of step (iii), the reaction is performed in the presence of an organic base. In some embodiments, the organic base is triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene or 1,5-diazabicyclo[4.3.0]undec-7-ene. In other embodiments, the organic base is triethylamine, diisopropylethylamine, N-methylmorpholine, or pyridine.

In other embodiments of step (iii), the reaction is performed in the absence of a base.

4.3. Method of Synthesis of 1-(Acyloxy)-Alkyl Carbamates

In another aspect, a method of synthesizing a 1-(acyloxy)-alkyl carbamate compound of Formula (III) is provided:

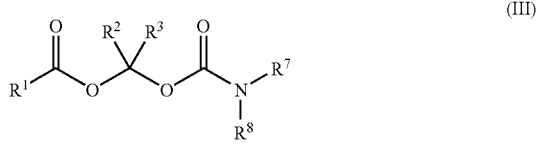

comprising:
(i) contacting a compound of Formula (IV) and a compound of Formula (V) to provide a compound of Formula (VI);
(ii) contacting the compound of Formula (VI) with a carboxylate compound of Formula (VII) to provide an acyloxyalkyl thiocarbonate compound of Formula (VIII);
(iii) contacting the thiocarbonate compound of Formula (VIII) with an oxidant (IX), in the presence of an N-hydroxysuccinimide compound of Formula (X) to afford the compound of Formula (I); and
(iv) contacting the compound of Formula (I) with a primary or secondary amine-containing drug of Formula (II) to afford a compound of Formula (III), or a pharmaceutically acceptable salt, hydrate or solvate thereof;

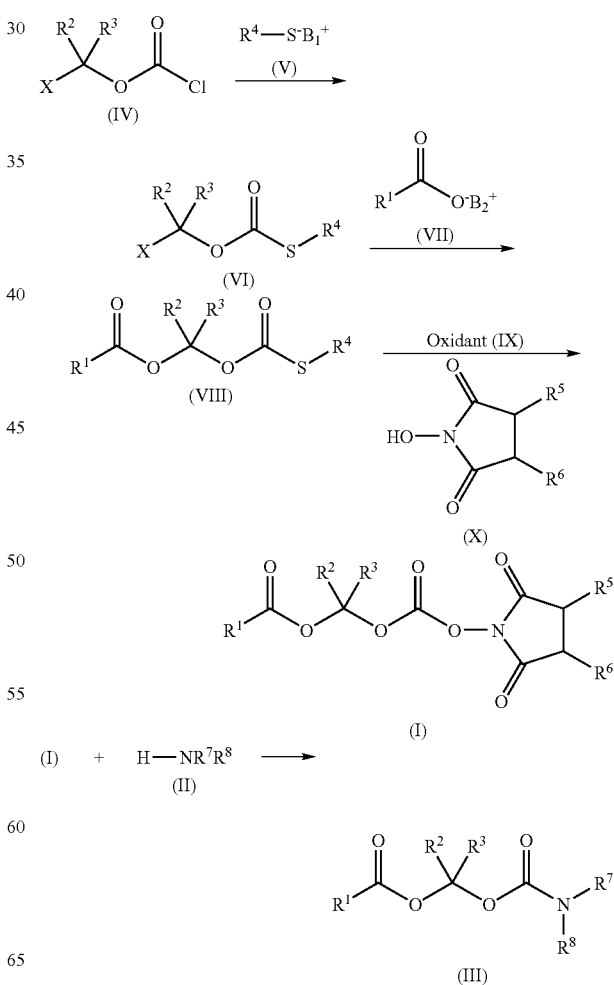

wherein HNR⁷R⁸ is a primary or secondary amine-containing drug, and each of X, $B_1^+$, $B_2^+$, and $R^1$ to $R^6$ are as described in Section 4.2.

Exemplary embodiments for X, $B_1^+$, $B_2^+$, $R^1$, $R^2$, $R^3$, $R^4$, $R^5$ and $R^6$ have been described in Section 4.2, above. Exemplary reaction conditions for the first three steps of the above method (i.e., molar ratio of reactants, reaction temperature, solvents, etc.) have also been described in Section 4.2 above.

Those of skill in the art will appreciate that the following embodiments, infra, refer to this method of synthesizing a 1-(acyloxy)-alkyl carbamate compound of Formula (III).

Examples of drugs HNR⁷R⁸ which contain primary or secondary amine groups include, but are not limited to, acebutalol, albuterol, alprenolol, atenolol, bunolol, bupropion, butopamine, butoxamine, carbuterol, cartelolol, colterol, deterenol, dexpropanolol, diacetolol, dobutamine, exaprolol, exprenolol, fenoterol, fenyripol, labotolol, levobunolol, metolol, metaproterenol, metoprolol, nadolol, pamatolol, penbutalol, pindolol, pirbuterol, practolol, prenalterol, primidolol, prizidilol, procaterol, propanolol, quinterenol, rimiterol, ritodrine, solotol, soterenol, sulfiniolol, sulfinterol, sulictidil, tazaolol, terbutaline, timolol, tiprenolol, tipridil, tolamolol, thiabendazole, albendazole, albutoin, alendronate, alinidine, alizapride, amiloride, aminorex, aprinocid, cambendazole, cimetidine, cisapride, clonidine, cyclobenzadole, delavirdine, efegatrin, etintidine, fenbendazole, fenmetazole, flubendazole, fludorex, gabapentin, icadronate, lobendazole, mebendazole, metazoline, metoclopramide, methylphenidate, mexiletine, neridronate, nocodazole, oxfendazole, oxibendazole, oxmetidine, pamidronate, parbendazole, pramipexole, prazosin, pregabalin, procainamide, ranitidine, tetrahydrazoline, tiamenidine, tinazoline, tiotidine, tocainide, tolazoline, tramazoline, xylometazoline, dimethoxyphenethylamine, N-[3(R)-[2-piperidin-4-yl)ethyl]-2-piperidone-1-yl]acetyl-3(R)-methyl-β-alamine, adrenolone, aletamine, amidephrine, amphetamine, aspartame, bamethan, betahistine, carbidopa, clorprenaline, chlortermine, dopamine, L-Dopa, ephrinephrine etryptamine, fenfluramine, methyldopamine, norepinephrine, tocainide, enviroxime, nifedipine, nimodipine, triamterene, pipedemic acid and similar compounds, 1-ethyl-6-fluoro-1,4-dihydro-4-oxo-7-(1-piperazinyl)-1,8-napthyridine-3-carboxylic acid and 1-cyclopropyl-6-fluoro-1,4-dihydro-4-oxo-7-(piperazinyl)-3-quinolinecarboxylic acid, theprubicin, deoxyspergualin, seglitide, nebracetam, benanomicin B, eremomycin, thrazarine, tosufloxacin, baogongteng A, angiopeptin, boholmycin, ravidomycin, tageflar, orienticins, amphotericin B, tiamdipine, doxorubicin, lysobactin, mofegiline, octreotide, oxolide, amikacin, phospholine, nuvanil, cispentacin, chlororetain, remacemide, ramoplanins, janthinomycins, mersacidin, droxidopa, helvecardin A, helvecardin B, rilmazafone, vigabatrin, amlodipine, (R)-(+)-amlodipine, mideplanin, milnacipran, pranedipine, olradipine, deoxymethylspergualin, fudosteine, trovafloxacin, ceranapril, restricticin, idarubicin, arbekacin, giracodazole, poststatin, pazufloxacin, D-cycloserine, ovothiol A, ceftizoxime, icatibant, p-iodorubidazone, aladapcin, dalargin, seproxetine, pradimicin E, pradimicin FA-2, tafenoquine, sampatrilat, ruboxyl, dactimicin, alatrofloxacin, galarubicin, metaraminol, exatecan, squalamine, paromomycin, leustroducsin A, leustroducsin B, leustroducsin C, lanicemine, azoxybacilin, tetrafibricin, pixantrone, ziconotide, garomefrine, spinorphin, doripenem, alestramustine, seraspenide, safingol, aminolevulinic acid, pelagiomicin C, styloguanidine, L-4-oxalysine, eglumegad, rhodopeptins, mycestericin E, midaxifylline, anisperimus, lagatide, ibutamoren, oritavancin, ecenofloxacin, metyrosine, methyldopa, baclofen, tranylcypromine, micromomicin, zorubicin, epirubicin, gilatide, epithalon, cystamine, pluraflavin A, pluraflavin B, pasireotide, caprazamycin, barusiban, spisulosine, 21-aminoepothilone B, capsavanil, olcegepant, sulphostin, lobophorin A, papuamide A, papuamide B, cystocin, deoxynegamycin, galnon, pyloricidin B, brasilicardin A, neramexane, kaitocephalin, icofungipen, aliskiren, capromorelin, histaprodifen, donitriptan, cambrescidins, tipifamib, tabimorelin, belactosin A, belactosin C, circinamide, targinine, sulphazocine, nepicastat, oseltamivir, hydrostatin A, butabindide, netamiftide, memantine, fluvoxamine, deferoxamine, tranexamic acid, fortimicin A, cefaclor, lisinopril, ubestatin, cefminox, aspoxicillin, cefcanel, cefcanel daloxate, olamufloxacin, R-(+)-aminoindane, gemifloxacin, kahalalide F, palau'amine, examorelin, leustroducsin H, sabarubicin, amifostine, L-homothiocitrulline, L-thiocitrulline, impentamine, neboglamine, amselamine, cetefloxacin, cyclothialidine, fluvirucin B2, loracarbef, cefprozil, sperabillins, milacainide, avizafone, .alpha.-methyl-tryptophan-, cytaramycin, lanomycin, decaplanin, eflomithine, L-histidinol, tuftsin, kanamycin, amthamine, sitafloxacin, leurubicin, amantadine, isodoxorubicin, gludopa, bactobolin, esafloxacin, tabilautide, lazabemide, enalkiren, amrubicin, daunorubicin, mureidomycins, pyridazomycin, cimaterol, (+)-isamoltan, N-desmethylmilameline, noberastine, fosopamine, adaprolol, pradimicin B, amosulalol, xamoterol, boholmycin, risotilide, indeloxazine, denopamine, parodilol, utibapril, nardeterol, biemnidin, sparfloxacin, sibanomicin, tianeptine, oberadilol, methoctramine, sezolamide, anabasine, zilpaterol, zabiciprilat, enkastins, ulifloxacin, (+)-sotalol, deoxynojirimycin, altromycin A, altromycin C, dorzolamide, fepradinol, delapril, ciprofloxacin, balofloxacin, mepindolol, berlafenone, ramipril, dopexamine, dilevalol, (−)-nebivolol, duramycin, enalapril, meluadrine, zelandopam, voglibose, sertraline, carvedilol, pafenolol, paroxetine, fluoxetine, phendioxan, saimeterol, solpecainol, repinotan, bambuterol, safinamide, tilisolol, 7-oxostaurosporine, caldaret, sertraline, cilazapril, benazepril, prisotinol, gatifloxacin, ovothiol B, adaprolol, tienoxolol, fluparoxan, alprenoxime, efegatran, pradimicin, salbostatin, ersentilide, (S)-noremopamil, esperamicin A1, batoprazine, ersentilide, osutidine, quinapril, dihydrexidine, argiopine, pradimicin D, frovatriptan, hispidospermidin, silodosin, michellamine B, sibenadet, tetrindol, talibegron, topixantrone, nortopixantrone, tecalcet, buteranol, .alpha.-methylepinephrine, nomicotine, thiofedrine, lenapenem, imidapril, epibatidine, premafloxacin, socorromycin, trandolapril, tamsulosin, dirithromycin, inogatran, vicenistatin, immepyr, immepip, balanol, orbifloxacin, maropitant, dabelotine, lerisetron, ertapenem, nolomirole, moxifloxacin, vofopitant, halofuginone, melagatran, ximelagatran, fasudil, isofagomine, pseudoephedrine, propafenone, celiprolol, carteolol, penbutolol, labetalol, acebutolol, reproterol, rimoterol, amoxapine, maprotiline, viloxazine, protriptyline, nortriptyline, desipramine, oxprenolol, propranolol, ketamine, butofilolol, flecainide, tulobuterol, befunolol, immucillin-H, vestipitant, cinacalcet, lapatinib, desloratadine, ladostigil, vildagliptin, tulathromycin B, becampanel, salbutamol, delucemine, solabegron, paroxetine, gaboxadol, telavancin, ralfinamide, tomoxetine, dalbavancin, elarofiban, ferulinolol, fenoldopam, sumanirole, sarizotan, brinzolamide, pradofloxacin, garenoxacin, reboxetine, ezlopitant, palindore, nebivolol, dinapsoline, proxodolol, repinotan, demexiptiline, mitoxantrone, norfloxacin, dilevalol, nipradilol, esmolol, ibopamine, troxipide, arotinolol, formoterol, bopindolol, cloranolol, mefloquine, perindopril, mabuterol, bisoprolol, bevantolol, betaxolol, tertatolol, enoxacin, lotrafiban, moexipril, droxinavir, adrogolide, alniditan, tigecycline, lubazodone, meropenem, temocapril, napsamycins, (−)-cicloprolol, ecteinascidins, alprafenone, landiolol, tirofiban, noberastine, rasagiline, setazindol, picumeterol, arbutamine, mecamylamine, imidapril, delfaprazine, midafotel, manzamines, binospirone, duloxetine, litoxetine. Many other secondary or primary amine drugs HNR$^7$R$^8$ are described in various compendia accessible to the skilled artisan, such as, for example, the Merck Index, 13$^{th}$ Edition, 2001, the Physciains Desk Reference, 59$^{th}$ Edition, 2005. Accordingly, secondary or primary amine drugs HNR$^7$R$^8$ described in the references, supra, are within the ambit of the present description.

In some embodiments, HNR$^7$R$^8$ is alendronate, amifostine, rac-baclofen, R-baclofen, carbidopa, clonidine, ciprofloxacin, cisapride, daunorubicin, doxorubicin, fenoldopam, fenoterol, gabapentin, gentamycin, kanamycin, levodopa, meropenem, metazoline, neomycin, pamidronate, pregabalin, tobramycin, trovafloxacin or vigabatrin. In other embodiments, HNR$^7$R$^8$ is gabapentin. In still other embodiments, HNR$^7$R$^8$ is R-baclofen. In still other embodiments, HNR$^7$R$^8$ is a GABA analog as defined herein.

In some embodiments, R$^2$ and R$^3$ in the compound of Formula (III) are different, such that the carbon atom to which R$^2$ and R$^3$ are attached is a stereogenic center.

In some embodiments, the compound of Formula (X) is chiral and non-racemic.

In some embodiments, R$^5$ and R$^6$ in the compound of Formula (X) are each benzoyloxy, the stereochemistry at the carbon to which R$^5$ is attached is of the R-configuration and the stereochemistry at the carbon to which R$^6$ is attached is of the R-configuration. In other embodiments, R$^5$ and R$^6$ in the compound of Formula (X) are each benzoyloxy, the stereochemistry at the carbon to which R$^5$ is attached is of the S-configuration, and the stereochemistry at the carbon to which R$^6$ is attached is of the S-configuration.

In some embodiments, R$^5$ and R$^6$ in the compound of Formula (X) are each isobutyroyloxy, the stereochemistry at the carbon to which R$^5$ is attached is of the R-configuration, and the stereochemistry at the carbon to which R$^6$ is attached is of the R-configuration. In other embodiments, R$^5$ and R$^6$ in the compound of Formula (X) are each isobutyroyloxy, the stereochemistry at the carbon to which R$^5$ is attached is of the S-configuration and the stereochemistry at the carbon to which R$^6$ is attached is of the S-configuration.

In some embodiments, R$^5$ and R$^6$ in the compound of Formula (X) are each pivaloyloxy, the stereochemistry at the carbon to which R$^5$ is attached is of the R-configuration, and the stereochemistry at the carbon to which R$^6$ is attached is of the R-configuration. In other embodiments, R$^5$ and R$^6$ in the compound of Formula (X) are each pivaloyloxy, the stereochemistry at the carbon to which R$^5$ is attached is of the S-configuration, and the stereochemistry at the carbon to which R$^6$ is attached is of the S-configuration.

In some embodiments, R$^5$ and R$^6$ in the compound of Formula (X) are each C$_{1-4}$ alkyl-substituted benzoyloxy, the stereochemistry at the carbon to which R$^5$ is attached is of the R-configuration and the stereochemistry at the carbon to which R$^6$ is attached is of the R-configuration. In other embodiments, R$^5$ and R$^6$ in the compound of Formula (X) are each C$_{1-4}$ alkyl-substituted benzoyloxy, the stereochemistry at the carbon to which R$^5$ is attached is of the S-configuration, and the stereochemistry at the carbon to which R$^6$ is attached is of the S-configuration.

In some embodiments, R$^2$ and R$^3$ in the compound of Formula (III) are different and the compound of Formula (I) comprises substantially one diastereomer.

In some embodiments, the drug HNR$^7$R$^8$ is a GABA analog of Formula (XI):

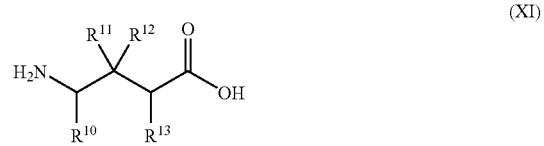

wherein:

R$^{10}$ and R$^{13}$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl; and R$^{11}$ and R$^{12}$ are independently selected from the group consisting of hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroarylalkyl and substituted heteroarylalkyl, or optionally, R$^{11}$ and R$^{12}$ together with the carbon atom to which they are attached form a cycloalkyl, substituted cycloalkyl, cycloheteroalkyl or substituted cycloheteroalkyl ring.

In some embodiments, the drug HNR$^7$R$^8$ is gabapentin, wherein R$^{10}$ and R$^{13}$ in Formula (XI) are each hydrogen, and where R$^{11}$ and R$^{12}$ together with the carbon atom to which they are attached form a cyclohexyl ring.

In some embodiments, R$^1$ is isopropyl, R$^2$ is methyl, R$^3$ is hydrogen, R$^4$ is methyl, ethyl or tert-butyl, R$^5$ and R$^6$ are each hydrogen and HNR$^7$R$^8$ is gabapentin.

In some embodiments, the drug HNR$^7$R$^8$ is baclofen, wherein R$^{10}$, R$^{12}$ and R$^{13}$ in Formula (XI) are each hydrogen, and where R$^{11}$ is 4-chlorophenyl. In other embodiments, the drug HNR$^7$R$^8$ is R-baclofen, wherein R$^{10}$, R$^{12}$ and R$^{13}$ in Formula (XI) are each hydrogen, R$^{11}$ is 4-chlorophenyl, and the stereochemistry at the carbon to which R$^{11}$ and R$^{12}$ are attached is of the R-configuration.

In some embodiments, R$^1$ is isopropyl, R$^2$ is isopropyl, R$^3$ is hydrogen, R$^4$ is methyl, ethyl or tert-butyl, R$^5$ and R$^6$ are each benzoyloxy and HNR$^7$R$^8$ is R-baclofen. In other embodiments, the compound of Formula (I) comprises substantially one diastereomer, wherein R$^1$ is isopropyl, R$^2$ is isopropyl, R$^3$ is hydrogen, and the stereochemistry at the carbon to which R$^2$ and R$^3$ are attached is of the S-configuration. In other embodiments, the compound of Formula (I) is substantially one diastereomer, wherein R$^1$ is isopropyl, R$^2$ is isopropyl, R$^3$ is hydrogen, and the stereochemistry at the carbon to which R$^2$ and R$^3$ are attached is of the R-configuration.

In some embodiments, R$^1$ is isopropyl, R$^2$ is isopropyl, R$^3$ is hydrogen, R$^4$ is methyl, ethyl or tert-butyl, R$^5$ and R$^6$ are each isobutyryloxy and HNR$^7$R$^8$ is R-baclofen. In other embodiments, the compound of Formula (I) is substantially one diastereomer, wherein R$^1$ is isopropyl, R$^2$ is isopropyl, R$^3$ is hydrogen, and the stereochemistry at the carbon to which R$^2$ and R$^3$ are attached is of the S-configuration. In still other embodiments, the compound of Formula (I) is substantially one diastereomer, wherein R$^1$ is isopropyl, R$^2$ is isopropyl, R$^3$ is hydrogen, and the stereochemistry at the carbon to which R$^2$ and R$^3$ are attached is of the R-configuration.

In some embodiments, R$^1$ is isopropyl, R$^2$ is isopropyl, R$^3$ is hydrogen, R$^4$ is methyl, ethyl or tert-butyl, R$^5$ and R$^6$ are each pivaloyloxy and HNR$_7$R$^8$ is R-baclofen. In other embodiments, the compound of Formula (I) is substantially one diastereomer, wherein $R^1$ is isopropyl, $R^2$ is isopropyl, $R^3$ is hydrogen, and the stereochemistry at the carbon to which $R^2$ and $R^3$ are attached is of the S-configuration. In still other embodiments, the compound of Formula (I) comprises substantially one diastereomer, wherein $R^1$ is isopropyl, $R^2$ is isopropyl, $R^3$ is hydrogen, and the stereochemistry at the carbon to which $R^2$ and $R^3$ are attached is of the R-configuration.

In some embodiments, $R^1$ is isopropyl, $R^2$ is isopropyl, $R^3$ is hydrogen, $R^4$ is methyl, ethyl or tert-butyl, $R^5$ and $R^6$ are each $C_{1-4}$ alkyl-substituted benzoyloxy and $HNR^7R^8$ is R-baclofen. In other embodiments, the compound of Formula (I) is substantially one diastereomer, wherein $R^1$ is isopropyl, $R^2$ is isopropyl, $R^3$ is hydrogen, and the stereochemistry at the carbon to which $R^2$ and $R^3$ are attached is of the S-configuration. In still other embodiments, the compound of Formula (I) is substantially one diastereomer, wherein $R^1$ is isopropyl, $R^2$ is isopropyl, $R^3$ is hydrogen, and the stereochemistry at the carbon to which $R^2$ and $R^3$ are attached is of the R-configuration.

In some embodiments, $HNR^7R^8$ is R-baclofen, $R^4$ is methyl, ethyl or tert-butyl, and the compound of Formula (I) is substantially one diastereomer, wherein $R^1$ is isopropyl, $R^2$ is isopropyl, $R^3$ is hydrogen, $R^5$ and $R^6$ are each benzoyloxy, the stereochemistry at the carbon to which $R^2$ and $R^3$ are attached is of the S-configuration, the stereochemistry at the carbon to which $R^5$ is attached is of the R-configuration, and the stereochemistry at the carbon to which $R^6$ is attached is of the R-configuration. In other embodiments, $HNR^7R^8$ is R-baclofen, $R^4$ is methyl, ethyl or tert-butyl and the compound of Formula (I) is substantially one diastereomer, wherein $R^1$ is isopropyl, $R^2$ is isopropyl, $R^3$ is hydrogen, $R^5$ and $R^6$ are each benzoyloxy, the stereochemistry at the carbon to which $R^2$ and $R^3$ are attached is of the R-configuration, the stereochemistry at the carbon to which $R^5$ is attached is of the S-configuration and the stereochemistry at the carbon to which $R^6$ is attached is of the S-configuration.

In some embodiments, $HNR^7R^8$ is R-baclofen, $R^4$ is methyl, ethyl or tert-butyl, and the compound of Formula (I) comprises substantially one diastereomer, wherein $R^1$ is isopropyl, $R^2$ is isopropyl, $R^3$ is hydrogen, $R^5$ and $R^6$ are each isobutyroyloxy, the stereochemistry at the carbon to which $R^2$ and $R^3$ are attached is of the S-configuration, the stereochemistry at the carbon to which $R^5$ is attached is of the S-configuration, and the stereochemistry at the carbon to which $R^6$ is attached is of the S-configuration. In other embodiments, $HNR^7R^8$ is R-baclofen, $R^4$ is methyl, ethyl or tert-butyl, and the compound of Formula (I) is substantially one diastereomer, wherein $R^1$ is isopropyl, $R^2$ is isopropyl, $R^3$ is hydrogen, $R^5$ and $R^6$ are each isobutyroyloxy, the stereochemistry at the carbon to which $R^2$ and $R^3$ are attached is of the R-configuration, the stereochemistry at the carbon to which $R^5$ is attached is of the R-configuration and the stereochemistry at the carbon to which $R^6$ is attached is of the R-configuration.

In some embodiments, fourth step of the above method is preferably carried out in a solvent. Solvents useful in step (iv) include, but are not limited to, acetone, acetonitrile, dichloromethane, dichloroethane, chloroform, toluene, tetrahydrofuran, dioxane, dimethylformamide, dimethylacetamide, N-methylpyrrolidinone, dimethyl sulfoxide, pyridine, ethyl acetate, methyl tert-butyl ether, methanol, ethanol, isopropanol, tert-butanol, water, or combinations thereof. In some embodiments, the solvent is acetone, acetonitrile, dichloromethane, toluene, tetrahydrofuran, pyridine, methyl tert-butyl ether, methanol, ethanol, isopropanol, water, or combinations thereof. In other embodiments, the solvent is a mixture of acetonitrile and water. In still other embodiments, the solvent is a mixture of acetonitrile and water, with a volume ratio of acetonitrile to water from about 1:5 to about 5:1. In still other embodiments, the solvent is a mixture of methyl tert-butyl ether and water. In still other embodiments, the solvent is a mixture of methyl tert-butyl ether and water, with a volume ratio of methyl tert-butyl ether to water from about 20:1 to about 2:1. In still other embodiments, the solvent is a mixture of methyl tert-butyl ether and water, wherein the methyl tert-butyl ether contains from about 10% to about 50% acetone by volume. In still other embodiments, the solvent is dichloromethane, water or a combination thereof. In still other embodiments, the solvent is a biphasic mixture of dichloromethane and water. In still other embodiments, the solvent is a biphasic mixture of dichloromethane and water containing from about 0.001 equivalents to about 0.1 equivalents of a phase transfer catalyst. In some embodiments, the phase transfer catalyst is a tetraalkylammonium salt. In other embodiments, the phase transfer catalyst is a tetrabutylammonium salt.

In some embodiments, step (iv) is carried out at a temperature between about −20° C. and about 40° C. In other embodiments, the temperature of step (iv) is between about −20° C. and about 25° C. In still other embodiments, the temperature of step (iv) is between about 0° C. and about 25° C. In still other embodiments, the temperature of step (iv) is between about 25° C. and about 40° C.

In some embodiments of step (iv), the reaction is performed in the absence of a base.

In other embodiments of step (iv), the reaction is performed in the presence of an inorganic base. In some embodiments, the inorganic base is an alkali metal bicarbonate or alkali metal carbonate salt. In other embodiments, the inorganic base is sodium bicarbonate.

In some embodiments of step (iv), the reaction is performed in the presence of an organic base. In some embodiments, the organic base is triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene or 1,5-diazabicyclo[4.3.0]undec-7-ene. In other embodiments, the organic base is triethylamine, diisopropylethylamine, N-methylmorpholine or pyridine.

In another aspect, a method of synthesizing a 1-(acyloxy)-alkyl carbamate compound of Formula (III) is provided:

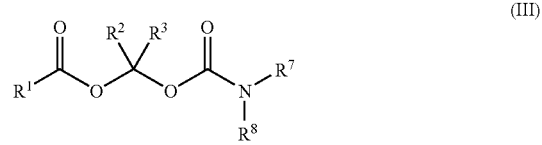

which comprises contacting a compound of Formula (I) with a primary or secondary amine-containing drug of Formula (II) to afford a compound of Formula (III), or a pharmaceutically acceptable salt, hydrate or solvate thereof;

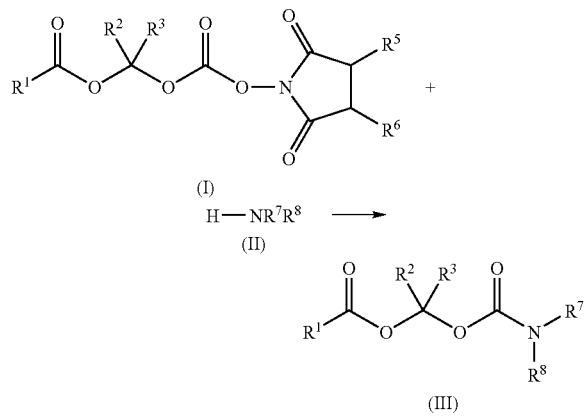

wherein $HNR^7R^8$ is a primary or secondary amine-containing drug as described above and $B_2^+$ is as described above and $R^1$ to $R^6$ are as described in Section 4.2.

Exemplary embodiments for $HNR^7R^8$, $B_2^+$, $R^1$, $R^2$, $R^3$, $R^4$, $R^5$ and $R^6$ have been either described above or in Section 4.2. Exemplary reaction conditions for the above method (i.e., molar ratio of reactants, reaction temperature, solvents, etc.) have also been described above.

In some embodiments, $HNR^7R^8$ is not a pseudomycin or pseudomycin analog or derivative as disclosed in Chen et al., International Publication No. WO 01/05183.

5. EXAMPLES

The invention is further defined by reference to the following examples, which describe in detail the preparation of 1-(acyloxy)-alkyl N-hydroxysuccinimidyl carbonates and illustrate methods of synthesizing 1-(acyloxy)-alkyl carbamate prodrugs. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

Atm=atmosphere
Boc=tert-butyloxycarbonyl
Cbz=carbobenzyloxy
DCC=dicyclohexylcarbodiimide
DMAP=4-N,N-dimethylaminopyridine
DMF=N,N-dimethylformamide
DMSO=dimethylsulfoxide
g=gram
h=hour
HPLC=high pressure liquid chromatography
L=liter
LC/MS=liquid chromatography/mass spectroscopy
M=molar
min=minute
mL=milliliter
mmol=millimoles
NHS=N-hydroxysuccinimide
THF=tetrahydrofuran
TFA=trifluoroacetic acid
TLC=thin layer chromatography
TMS=trimethylsilyl
μL=microliter
μM=micromolar
v/v=volume to volume

5.1 Example 1 O-(1-Chloroethyl) S-Methyl Thiocarbonate (1)

A solution of methanethiol (170 g, 3.5 mol) and 1-chloroethyl chloroformate (386 mL, 502 g, 3.5 mol) in $CH_2Cl_2$ (1 L) was cooled to 0° C. in an ice-water bath. N-Methylmorpholine (388 mL, 357 g, 3.53 mol) was added dropwise over a period of 1 h and the reaction mixture was allowed to stir at room temperature for 16 h. The reaction mixture was diluted with $CH_2Cl_2$ (2 L), washed with water (1 L), saturated bicarbonate solution (1 L) and brine (1 L), then dried over anhydrous sodium sulfate, filtered and concentrated in vacuo. The residue was purified by vacuum distillation (95° C./20 Torr) to provide the title compound (1) as colorless liquid (510 g, 94% yield). $^1$H NMR ($CDCl_3$, 400 MHz): δ 1.82 (d, J=5.6 Hz, 3H), 2.38 (s, 3H), 6.57 (q, J=5.2 Hz, 1H).

In an alternative synthesis of (1) a solution of methanethiol (170 g, 3.53 mol) and 1-chloroethyl chloroformate (505 g, 3.53 mol) in $CH_2Cl_2$ (1 L) was cooled to 0-4° C. in an ice-water bath. To the mixture was added a solution of triethylamine (357.6 g, 3.53 mol) in $CH_2Cl_2$ (1 L) dropwise over 2 h. The reaction was removed from the ice bath and stirred at ambient temperature for 2 h. The reaction was washed with water (3×1 L), the organic phase was separated, dried over anhydrous magnesium sulfate and concentrated in vacuo. The residue was purified by vacuum distillation to afford the product as a colorless liquid (500 g, 91.5%).

In another alternative synthesis of (1), a 21% (w/w) aqueous solution of sodium methylthiolate (580.7 g, 1.74 mol) was added to a solution of 1-chloroethyl chloroformate (250 g, 1.74 mol) and tetrabutylammonium hydrogensulfate (5.9 g, 17 mmol) in $CH_2Cl_2$ (450 mL) over 2 h. The reaction mixture was stirred for an additional hour, then worked-up by separating the aqueous phase and extracting the organic phase with brine (2×250 mL). The organic phase was dried over anhydrous sodium sulfate and concentrated in vacuo. The residue was purified by vacuum distillation to afford the product as a colorless liquid (277.3 g, 97%).

5.2 Example 2 O-(1-Chloroethyl) S-Ethyl Thiocarbonate (2)

A solution of 1-chloroethyl chloroformate (71.5 g, 0.5 mol) in diethyl ether (600 mL) was cooled to 0-4° C. in an ice-water bath and a solution of ethanethiol (37 mL, 0.5 mol) and triethylamine (69.3 mL, 0.5 mol) in diethyl ether (200 mL) was added dropwise over 1 h. The reaction mixture was removed from the ice bath and stirred at ambient temperature for 4 h. Triethylamine hydrochloride was removed by filtration, the filtrate concentrated under reduced pressure and the residue purified by vacuum distillation (67-68° C. at 240 mTorr) to afford the title compound (2) as a colorless liquid (75 g, 89%). $^1$H NMR ($CDCl_3$, 400 MHz): δ 1.35 (t, 3H), 1.8 (d, 3H), 2.9 (dq, 2H), 6.6 (q, 1H).

5.3 Example 3 O-(1-Chloroethyl) S-tert-Butyl Thiocarbonate (3)

A solution of tert-butyl thiol (180 g, 2 mol) and 1-chloroethyl chloroformate (284 g, 2 mol) in $CH_2Cl_2$ (1 L) was cooled to 0° C. in an ice-water bath. N-Methylmorpholine (212.1 g, 2.1 mol) was added dropwise over a period of 1 h and the reaction mixture was allowed to stir at room temperature for 16 h. The reaction mixture was diluted with excess CH$_2$Cl$_2$ (2 L), washed with water (2×1 L), saturated bicarbonate solution (1 L) and brine (1 L), dried over anhydrous sodium sulfate, filtered and concentrated in vacuo. The residue was purified by vacuum distillation (135° C./20 Torr) to provide the title compound (3) as a colorless liquid (350 g, 89%). $^1$H NMR (CDCl$_3$, 400 MHz): δ 1.50 (s, 9H), 1.79 (d, J=6 Hz, 3H), 6.57 (q, J=5.6 Hz, 1H).

5.4 Example 4 O-(1-Chloroethyl) S-Phenyl Thiocarbonate (4)

A solution of benzenethiol (50 g, 450 mmol) and 1-chloroethyl chloroformate (65 g, 450 mmol) in CH$_2$Cl$_2$ (300 mL) was cooled to 0-4° C. in an ice-water bath. To the mixture was added a solution of triethylamine (450 mmol) in dichloromethane (200 mL) dropwise over 30 min. The reaction was removed from the ice bath and stirred at ambient temperature for 12 h. The reaction was washed with water (3×500 mL), the organic phase was separated, dried over anhydrous magnesium sulfate and concentrated in vacuo to afford the product as a pale yellow liquid (96 g, 98.5%). $^1$H NMR (CDCl$_3$, 400 MHz): δ 1.82 (d, 3H), 6.6 (q, 1H), 7.2-7.4 (m, 5H).

5.5 Example 5 Tetrabutylammonium Isobutyrate (5)

A 40 wt % solution of tetrabutylammonium hydroxide in water (250 mL, 99 g, 382 mmol), water (300 mL) and isobutyric acid (33.8 g, 382 mmol) was stirred at ambient temperature for 30 min. The solvent was removed in vacuo to afford the title compound (5) as a waxy solid, which was used without further purification.

Alternatively, a 1M solution of tetrabutylammonium hydroxide in methanol (1 L, 1 mol) and isobutyric acid (88.5 g, 1 mol) was stirred at ambient temperature for 30 min. The solvent was removed in vacuo to afford the title compound (5) as a waxy solid, which was used without further purification.

5.6 Example 6

O-(1-Isobutanoyloxyethyl) S-Methyl Thiocarbonate (6)

Compound (1) (308 mg, 2 mmol) was dissolved in isobutyric acid (264 mg, 3 mmol). This mixture was slowly added to a pre-mixed solution of isobutyric acid (264 mg, 3 mmol) and diisopropylethylamine (387 mg, 3 mmol) and the reaction mixture heated to 55° C. for 16 h, diluted with ether (50 mL), washed with water (2×10 mL), saturated bicarbonate solution (2×10 mL) and brine (10 mL), then dried over anhydrous sodium sulfate, filtered and concentrated in vacuo to give the title compound (6) as colorless liquid (400 mg, 97%). The product was further purified by vacuum distillation (135° C./20 Torr). $^1$H NMR (CDCl$_3$, 400 MHz): δ 1.17 (d, J=6.8 Hz, 6H), 1.49 (d, J=5.6 Hz, 3H), 2.33 (s, 3H), 2.54 (m, 1H), 6.91 (q, J=5.2 Hz, 1H).

In an alternative synthesis of (6), a solution of compound (1) (154.6 g, 1 mol), isobutyric acid (1.53 mol), 40 wt % aqueous tetrabutylammonium hydroxide (1 L, 1.53 mol), and tetrahydrofuran (500 mL) was stirred at ambient temperature for 48 h. The reaction mixture was diluted with diethyl ether (1 L) and washed with water (2×3 L). The organic phase was separated, dried over anhydrous magnesium sulfate, filtered and concentrated in vacuo. The residue was purified by vacuum distillation (135° C./20 Torr) to afford the product as a colorless liquid (150 g, 73.5%).

5.7 Example 7 O-(1-isobutanoyloxyethyl) S-Ethyl Thiocarbonate (7)

To a solution of tetrabutylammonium isobutyrate (5) (382 mmol) in tetrahydrofuran (500 mL) was added compound (2) (49 g, 288 mmol). The mixture was stirred at ambient temperature for 16 h then the solvent removed in vacuo. The residue was dissolved in diethyl ether (600 mL), washed with water (3×300 mL) and the organic phase was separated, dried over anhydrous magnesium sulfate, filtered and concentrated in vacuo. The residue was purified by vacuum distillation (60° C./240 mTorr) to afford the product (7) as a colorless liquid (40 g, 63%). $^1$H NMR (CDCl$_3$, 400 MHz): δ 1.2 (d, 6H), 1.35 (t, 3H), 1.5 (d, 3H), 1.55 (m, 1H), 2.85 (dq, 2H), 6.95 (q, 1H).

5.8 Example 8 O-(1-Isobutanoyloxyethyl) S-tert-Butyl Thiocarbonate (8)

Compound (3) (392 mg, 2 mmol) was dissolved in isobutyric acid (264 mg, 3 mmol) and the solution was slowly added to a pre-mixed solution of isobutyric acid (264 mg, 3 mmol) and diisopropylethylamine (387 mg, 3 mmol). The reaction mixture was heated to 55° C. for 16 h, then diluted with ether (50 mL), washed with water (2×10 mL), saturated bicarbonate solution (2×10 mL) and brine (10 mL), dried over anhydrous sodium sulfate, filtered and concentrated in vacuo to give the title compound (8) as a colorless liquid (450 mg, 90%). The product was further purified by vacuum distillation (170° C./20 Torr). $^1$H NMR (CDCl$_3$, 400 MHz): δ 1.16 (d, J=7.2 Hz, 6H), 1.47 (s, 9H), 1.48 (d, J=5.6 Hz, 3H), 2.53 (m, 1H), 6.90 (q, J=5.2 Hz, 1H).

5.9 Example 9 O-(1-Isobutanoyloxyethyl) S-Phenyl Thiocarbonate (9)

A mixture of compound (4) (10 g, 46 mmol), isobutyric acid (30 mL), triethylamine (30 mL) and sodium iodide (2 g) was stirred and heated in an oil bath at 50° C. for 3 days. The reaction mixture was diluted with diethyl ether (200 mL) and washed successively with water (3×100 mL), saturated aqueous sodium bicarbonate (2×100 mL) and 0.1 M aqueous potassium bisulfate (2×100 mL). The organic phase was separated, then dried over anhydrous magnesium sulfate, filtered and concentrated in vacuo to give the title compound (9) as a pale yellow liquid (12 g, 97%). $^1$H NMR (CDCl$_3$, 400 MHz): δ 1.2 (d, 6H), 1.5 (d, 3H), 2.55 (m, 1H), 6.95 (q, 1H), 7.4-7.5 (m, 5H).

5.10 Example 10

[(1-Isobutanoyloxyethoxy)carbonyloxy] Succinimide (10)

To a solution of compound (6) (1 g, 4.8 mmol) in CH$_2$Cl$_2$ (10 mL) was added N-hydroxysuccinimide (1.1 g, 9.5 mmol) and the reaction mixture cooled to 0° C. A solution of 32% (v/v) peracetic acid in acetic acid (3.4 mL, 1.1 g, 14.4 mmol) was added dropwise over a period of 10 mm, then the solution allowed to stir at room temperature for 3 h. The reaction mixture was diluted with ether (50 mL) and washed with water (2×10 mL), saturated sodium bicarbonate solution (10 mL) and brine (10 mL), then dried over anhydrous sodium sulfate, filtered and concentrated in vacuo to give the title compound (10) as a as colorless oil (1 g, 77%). After trituration with hexane (20 mL) the product solidified to a white solid. m.p: 50-54° C. $^1$H NMR (CDCl$_3$, 400 MHz): δ 1.17 (d, J=6.8 Hz, 6H), 1.56 (d, J=5.6 Hz, 3H), 2.55 (m, 1H), 2.82 (s, 4H), 6.80 (q, J=5.2 Hz, 1H). MS (ESI) m/z 296.4 (M+Na)$^+$.

In an alternative synthesis of (10), N-hydroxysuccinimide (558 mg, 4.8 mmol) was added to a solution of compound (6) (500 mg, 2.4 mmol) in $CH_2Cl_2$ (10 mL) and the reaction mixture cooled to 0° C. m-Chloroperbenzoic acid (1.62 g, 7.2 mmol, commercial grade: 77% in water) was added over a period of 10 min and the mixture allowed to stir at room temperature for 16 h. The reaction mixture was diluted with ether (50 mL) and washed with water (2×10 mL), saturated sodium bicarbonate solution (10 mL) and brine (10 mL). The organic layer was dried over anhydrous sodium sulfate, filtered and concentrated in vacuo to give the title compound (10) together with m-chlorobenzoic acid. The crude product mixture was purified by column chromatography on silica gel, eluting with 4:6 EtOAc: hexane. Residual m-chlorobenzoic acid was removed by repeated crystallizations from a mixture of tert-butyl methyl ether and hexane, resulting in analytically pure product (66 mg, 10%).

In an alternative synthesis of (10), a 500-mL, three-neck flask equipped with a mechanical stirrer, teflon-coated thermocouple and a nitrogen inlet was charged with compound (6) (16.6 g, 0.08 mol), N-hydroxysuccinimde (11.04 g, 0.096 mol), magnesium monoperoxyphthalate (80% technical grade; 110 g, ~2.3 equivalent of active oxidant) and $CH_2Cl_2$ (180 mL). The resulting white suspension was stirred for 5 h at 20-25° C. The reaction mixture was filtered and the filter-cake was slurried and washed with $CH_2Cl_2$ (3×300 mL). The slurry was filtered and the organic phase was washed with water (300 mL). The organic layer was then stirred twice with 20% aq. $K_2CO_3$ solution (2×300 mL) for 10 min to remove phthalic acid, and finally with brine (300 mL). The organic layer was dried over anhydrous $Na_2SO_4$ and concentrated to give the title compound (10) as a viscous product (18.0 g, 82%) which solidified on standing.

In another alternative synthesis of (10), a solution of trifluoroacetic anhydride (2 mL, 14.5 mmol) in $CH_2Cl_2$ (10 mL) was added to a stirred suspension of urea-hydrogen peroxide complex (2.74 g, 29.1 mmol) and sodium bicarbonate (4 g, 48.5 mmol) in anhydrous $CH_2Cl_2$ (80 mL) under a nitrogen atmosphere at 0° C. The resulting mixture was allowed to stir at 0° C. for 30 min. N-Hydroxysuccinimide (1.1 g, 9.7 mmol) was added to the reaction mixture at 0° C., followed by the addition of a solution of compound (6) (1 g, 4.85 mmol) in $CH_2Cl_2$ (10 mL), then the reaction mixture was warmed to ambient temperature with stirring for 16 h. The reaction mixture was decanted and the solvent was removed in vacuo. The colorless residue was dissolved in ethyl acetate (100 mL) and washed with water (1×50 mL) and brine (1×50 mL). The organic layers were pooled and dried over anhydrous magnesium sulfate and the solvent was removed in vacuo to afford the title compound (10) as a clear oil (1 g, 75%), which solidified after pumping under high vacuum.

In another alternative synthesis of (10), a solution of acetic anhydride (2 mL) in $CH_2Cl_2$ (10 mL) was added to a stirred suspension of urea-hydrogen peroxide complex (2.74 g, 29.1 mmol) and sodium bicarbonate (4 g, 48.5 mmol) in anhydrous $CH_2Cl_2$ (80 mL) under a nitrogen atmosphere at 0° C. The resulting mixture was allowed to stir at 0° C. for 30 min. N-Hydroxysuccinimide (1.1 g, 9.7 mmol) was added to the reaction mixture at 0° C., followed by the addition of a solution of compound (6) (1 g, 4.85 rumol) in $CH_2Cl_2$ (10 mL), then the reaction mixture was stirred at 40° C. for 16 h. The reaction mixture was decanted and the solvent was removed in vacuo. The colorless residue was dissolved in ethyl acetate (100 mL) and washed with water (1×50 mL) and brine (1×50 mL). The organic layers were pooled and dried over anhydrous magnesium sulfate and the solvent was removed in vacuo to afford the title compound (10) as a clear oil which solidified after pumping under high vacuum.

In another alternative synthesis of (10), to a well-stirred suspension of urea-hydrogen peroxide complex (47 g, 0.5 mol) and N-hydroxysuccinimide (13.8 g, 0.12 mol) in dichloromethane (100 mL) was added solid maleic anhydride (29.4 g, 0.3 mol). The mixture was stirred at room temperature for 15 min and then a solution of compound (6) (20.6 g, 0.1 mol) in dichloromethane (50 mL) was added slowly over a period of 15 min. The reaction proceeded with an exotherm that could be controlled by using a water bath for cooling. The reaction mixture was stirred at 20-25° C. for 4 h, during which time a white precipitate formed. The reaction mixture was diluted with water (200 mL) and the phases separated. The aqueous layer was extracted with dichloromethane (200 mL), the combined organic layers were washed with brine (200 mL) and dried over anhydrous $Na_2SO_4$. The solvent was removed in vacuo to afford the title compound (10) as a white crystalline solid (20.0 g, 73% yield).

In still another alternative synthesis of (10), N-hydroxysuccinimide (2.3 g, 20 mmol) was added to a solution of compound (8) (1 g, 4 mmol) in $CH_2Cl_2$ (10 mL) and the reaction mixture cooled to 0° C. A solution of 32% (v/v) peracetic acid in acetic acid (0.92 g, 12 mmol) was added dropwise over a period of 10 min, then the solution was allowed to stir at room temperature for 3 h. The reaction mixture was diluted with ether (50 mL) and washed with water (2×10 mL), saturated sodium bicarbonate solution (10 mL) and brine (10 mL), then dried over anhydrous sodium sulfate, filtered, and concentrated in vacuo to give the title compound (10) as a as colorless oil (0.9 g, 81%). After trituration with hexane (20 mL) the product solidified to provide a white solid.

In still another alternative synthesis of (10), N-hydroxysuccinimide (230 mg, 2 mmol) was added to a solution of compound (8) (248 mg, 1 mmol) in $CH_2Cl_2$ (10 mL) was added and the reaction mixture cooled to 0° C. m-Chloroperbenzoic acid (670 mg, 3 mmol, commercial grade: 77% in water) was added over a period of 10 min and the mixture allowed to stir at room temperature for 16 h. The reaction mixture was diluted with ether (50 mL) and washed with water (2×10 mL), saturated sodium bicarbonate solution (10 mL) and brine (10 mL). The organic layer was dried over anhydrous sodium sulfate, filtered and concentrated in vacuo to give the title compound (10) together with m-chlorobenzoic acid. The crude product mixture was purified by column chromatography on silica gel, eluting with 4:6 EtOAc: hexane. Residual m-chlorobenzoic acid was removed by repeated crystallizations from a mixture of tert-butyl methyl ether and hexane which resulted in analytically pure product (30 mg, 11%).

In still another alternative synthesis of (10), a 500-mL three-neck flask equipped with a mechanical stirrer, teflon-coated thermocouple and addition funnel was charged with compound (8) (20.6 g, 0.1 mol), N-hydroxysuccinimde (23.0 g, 0.2 mol) and $CH_2Cl_2$ (80 mL). The reaction mixture was cooled to 0° C. and peracetic acid (32% solution in acetic acid, 16.7 g, 55 mL, 0.22 mol) added dropwise to the reaction mixture at a rate such that the temperature remained below 5° C. Upon completion of the addition, the reaction mixture was stirred for 4.5 h, maintaining the temperature at or below 15° C. The reaction mixture was then cooled to 0° C. and neutralized with 10% aqueous $K_2CO_3$ until the pH of the reaction mixture was ~7. The mixture was then extracted with $CH_2Cl_2$ (2×100 mL) and the combined $CH_2Cl_2$ phases were washed with brine and dried over anhydrous sodium sulfate. The organic phase was then concentrated, affording the crude product as a white solid (20.2 g, 75%). This solid was recrystallized by dissolution in isopropanol (41 mL), warming the mixture to 40° C. to afford a homogeneous solution. The solution was cooled to 0° C. over two hours and the product was filtered and dried, resulting in recovery of the title compound (10) as a white solid (16 g, 79%) having a melting point of 54-56° C.

5.11 Example 11 Tetrabutylammonium 1-Aminomethyl-1-Cyclohexane Acetate (11)

A solution containing gabapentin (34.4 g, 200 mmol), a 1 M solution of tetrabutylammonium hydroxide in methanol (200 mL, 200 mmol), and additional methanol (200 mL) was stirred at ambient temperature for 14 h. The solvent was removed in vacuo, then toluene (200 mL) was added and evaporated under reduced pressure two times. The title compound (11) was obtained as a thick syrup, and was further dried under high vacuum and used without further purification.

5.12 Example 12

{[(1-Isobutanoyloxyethoxy)carbonyl]aminomethyl}-1-Cyclohexane Acetic Acid (12)

To a solution of gabapentin (1.7 g, 10 mmol) and sodium bicarbonate (20 mmol) in water (40 mL) was added a solution of compound (10) (2.73 g, 10 mmol) in acetonitrile (20 mL) over 1 min. The reaction was stirred at ambient temperature for 16 h. The reaction mixture was diluted with diethyl ether (100 mL) and washed with 0.1 M aqueous potassium bisulfate (3×100 mL). The organic phase was separated, dried over anhydrous magnesium sulfate, filtered, and concentrated in vacuo to afford the title compound (12) as a white solid (2.7 g, 96%). The product was recrystallized by dissolution in 1:10 ethyl acetate: heptane (10 mL) at 60° C., followed by slow cooling to 4° C. The white crystalline product was isolated by filtration. Melting point: 63-64° C. $^1$H NMR (CDCl$_3$, 400 MHz): 1.15 (d, 6H), 1.40-1.55 (m, 10H), 1.45 (d, 3H), 2.32 (s, 2H), 2.49-2.56 (m, 1H), 3.23 (d, 2H), 5.41 (t, 1H), 6.75 (q, 1H). MS(ESI) m/z 330.29 (M+H$^+$).

In an alternative synthesis of (12), a 1-L three-necked flask equipped with a mechanical stirrer, nitrogen inlet and temperature probe was charged with compound (10) (100 g, 0.36 mol), gabapentin (68.9 g, 0.40 mol), methyl tert-butyl ether (300 mL) and water (30 mL). The suspension was stirred at room temperature and become a clear biphasic mixture after 1.5 h. After 6 h the phases were separated and the aqueous phase extracted with additional methyl tert-butyl ether (400 mL). The organic phases were combined and washed with saturated brine solution (3×100 mL). The clear organic phase was concentrated in vacuo to yield an oil that crystallized overnight under high vacuum. The title compound (12) was collected as a white solid (120 g, 99.5% yield).

In an alternative synthesis of (12), a solution containing compound (11) (4.1 g, 10 mmol) and compound (10) (2.73 g, 10 mmol) in toluene (40 mL) was stirred at ambient temperature for 1 h. The reaction mixture was diluted with diethyl ether (100 mL) and washed with 0.1 M aqueous potassium bisulfate (3×100 mL). The organic phase was separated, dried over anhydrous magnesium sulfate, filtered and concentrated in vacuo to afford the title compound (12) as a white solid (2.6 g, 93%).

5.13 Example 13 Synthesis of O-(1-Isobutanoyloxyisobutoxy) S-Methyl Thiocarbonate (13)

Step A: O-(1-Chloroisobutoxy) S-Methyl Thiocarbonate (14)

A solution of 1-chloro-2-methylpropyl chloroformate (1026 g, 6.0 mol) and tetrabutylammonium hydrogensulfate (20 g, 60 mmol) in dichloromethane (1500 mL) in a jacketed 10 L reactor equipped with a mechanical stirrer, temperature probe, and addition funnel was cooled to 10° C. To the reaction mixture was gradually added a 15% aqueous solution of sodium methylthiolate (3 L, 6.4 mol) over 4 h. The reaction was moderately exothermic and the internal temperature was maintained between 10 and 20° C. during the addition. The aqueous phase was separated and the organic phase was washed with brine (2×2 L) and water (2 L). The organic layer was dried over anhydrous Na$_2$SO$_4$, filtered, and concentrated under reduced pressure to afford the title compound (14) (1050 g, 5.76 mol, 96%) as a colorless liquid. $^1$H NMR (CDCl$_3$, 400 MHz): δ 1.1 (dd, 6H), 2.2 (m, 1H), 2.4 (s, 3H), 6.35 (d, 1H).

Step B: Tetramethylammonium Isobutyrate (15)

To a 20 L round bottom flask was added isobutyric acid (1300 mL, 14 mol), and an aqueous solution of 25% tetramethylammonium hydroxide (5 L, 14 mol). The water was removed under reduced pressure, and azeotroped with toluene (2×2 L) to leave the product (15) as an amber liquid, which was used without further purification.

Step C: O-(1-Isobutanoyloxyisobutoxy) S-Methyl Thiocarbonate (13)

To a 3 L three neck round bottom flask equipped with a mechanical stirrer and teflon-coated thermocouple was added (15) (1672 g, 9 mol), isobutyric acid (264 g, 1.5 mol), and (14) (1050 g, 5.76 mol). The reaction mixture was heated to 80° C. for 12 h, monitoring the reaction progress by $^1$H NMR. The reaction mixture was cooled to 20° C., diluted with EtOAc (1 L) and washed with water (2×1 L), saturated NaHCO$_3$ (1×2 L) and water (1 L). The organic phase was separated and concentrated under reduced pressure to afford the product (13) (905 g, 3.9 mol, 65%) as a colorless liquid. $^1$H NMR (CDCl$_3$, 400 MHz): δ 1.0 (d, 6H), 1.2 (dd, 6H), 2.05 (m, 1H), 2.35 (s, 3H), 2.6 (m, 1H), 6.7 (d, 1H).

5.14 Example 14 Synthesis of (1R)-1-[((3S,4S)-2,5-Dioxo-3,4-dibenzoyloxypyrrolidinyl)-oxycarbonyloxy]-2-methylpropyl 2-methylpropanoate (16)

Step A: (3S,4S)-2,5-Dioxo-3,4-dibenzoyloxy-3,4-dihydrofuran (17)

A suspension of 2,3-dibenzoyl-D-tartaric acid (100 g, 279 mmol) in acetic anhydride (300 mL) was stirred at 85° C. for 2 h then the reaction mixture was allowed to cool to room temperature. The crystalline product was collected by filtration, washed with a mixture of ether and hexane (1:1) and dried under vacuum to afford the title compound (17) (80 g, 84%). $^1$H NMR (CDCl$_3$, 400 MHz): δ 5.99 (s, 2H), 7.50 (m, 4H), 7.66 (m, 2H), 8.07 (m, 4H).

Step B: 1-Hydroxy-(3S,4S)-2,5-Dioxo-3,4-dibenzoyloxy-pyrrolidine (18)

To a suspension of (17) (60 g, 176 mmol) in a mixture of acetonitrile and water (8:1, 400 mL) at 0° C. was added a 50% aqueous solution of hydroxylamine (13.0 mL, 211 mmol). The resulting suspension was stirred overnight at room temperature to obtain a clear solution. The bulk of the acetonitrile was removed by rotary evaporation and the residue was portioned between ethyl acetate and water. The organic phase was washed successively with water and brine, dried over anhydrous $Na_2SO_4$ and concentrated in vacuo to afford the intermediate, 2,3-dibenzoyloxy D-tartaric acid mono-hydroxamate. This compound was suspended in toluene heated under reflux for 2 h, then cooled to room temperature to form a crystalline solid. The product was collected by filtration, washed with a mixture of ether and hexane (1:1), and dried under vacuum to afford the title compound (18) (58 g, 93%). $^1H$ NMR ($CDCl_3$, 400 MHz): δ 6.06 (s, 2H), 7.50 (t, 4H), 7.65 (dt, 2H), 8.06 (m, 4H). MS (ESI) m/z 354.00 (M−H)$^-$.

Step C: (1R)-1-[((3S,4S)-2,5-Dioxo-3,4-dibenzoyloxypyrrolidinyl)-oxycarbonyloxy]-2-methylpropyl 2-methylpropanoate (16)

To a stirred solution of compound (18) (35 g, 98.6 mmol) and thiocarbonate (13) (34.6 g, 148 mmol) in dichloromethane at 0° C. was dropwise added a 32% solution of peracetic acid (300 mmol) in acetic acid over 2 h. The reaction temperature was kept below 35° C. during the addition of peracetic acid. After the addition was complete, the reaction mixture was stirred overnight at room temperature. The resulting white precipitate was filtered and washed successively with water, and a mixture of ether and hexane (1:2), then dried under vacuum to afford the crude title compound. This product was crystallized once from a mixture of ethyl acetate and hexane (1:1) to afford the title compound (16) (13.7 g, 25%). The diastereomeric purity of the product was determined to be 98.4% d.e. by HPLC using a chiral column. $^1H$ NMR ($CDCl_3$, 400 MHz): δ 1.06 (d, 6H), 1.22 (d, 3H), 1.22 (d, 3H), 2.20 (m, 1H), (hept. 1H), 6.01 (br. s, 2H), 6.64 (d, 1H), 7.47 (m, 4H), 7.63 (m, 2H), 8.07 (m, 4H).

5.15 Example 15 Synthesis of 4-{[(1R)-Isobutanoyloxyisobutoxy]carbonylamino}-(3R)-(4-chlorophenyl)-butanoic Acid (19)

To a stirred suspension of (16) (11.7 g, 21.7 mmol) in a mixture of THF and water (10:1) (220 mL) at room temperature was added R-baclofen (4.78 g, 22.5 mmol). The resulting reaction mixture was stirred until the suspension became a clear solution (ca. 2 h) then was concentrated in vacuo to remove most of the solvent. The residue was partitioned between ether and water, the ether layer was washed with water and brine, and dried over anhydrous $Na_2SO_4$. After filtration and concentration in vacuo, the crude product was obtained and then purified by flash-chromatography on silica gel, eluting with a gradient of 10-20% acetone in hexane. Crystallization from an acetone/hexane mixture afforded the title compound (19) (8.22 g, 95% yield). The diastereomeric purity of the product was determined to be 99.9% d.e. by HPLC using a chiral column. $^1H$ NMR ($CDCl_3$, 400 MHz): δ 0.95 (d, 6H), 1.17 (d, 3H), 1.18 (d, 3H), 1.99 (m, 1H), 2.55 (hept. 1H), 2.64 (dd, 1H), 2.76 (dd, 1H), 3.40 (m, 3H), 4.73 (br. t, 1H), 6.51 (d, 1H), 7.13 (d, 2H), 7.27 (m, 2H). MS (ESI) m/z 398.50 (M−H)$^-$.

5.16 Example 16 Synthesis of Sodium 4-{(1R)-Isobutanoyloxyisobutoxylcarbonylamino}-(3R)-(4-chlorophenyl)-butanoate (20)

The carboxylic acid (19) was converted to the sodium salt by dissolution in MeCN (0.5 mL) and then addition of aqueous $NaHCO_3$ (1 eq.) with sonication for 15 min. The solvent was removed by lyophilization to afford the title compound (20). $^1H$ NMR ($CD_3OD$, 400 MHz): δ 0.93 (d, 3H), 0.94 (d, 3H), 1.94 (m, 1H), 1.08 (d, 3H), 1.10 (d, 3H), 2.37-2.54 (m, 3H), 3.31 (m, 3H), 6.43 (d, 1H), 7.23 (s, 4H). MS (ESI) m/z 398.57 (M−Na)$^-$.

5.17 Example 17 Synthesis of (1S-1-[((3R,4R)-2,5-Dioxo-3,4-dibenzoyloxypyrrolidinyl)-oxycarbonyloxy]-2-methylpropyl 2-methylpropanoate (21)

Step A: (3R,4R)-2,5-Dioxo-3,4-dibenzoyloxy-3,4-dihydrofuran (22)

To a 3-necked 5 L round bottom flask fitted with a mechanical stirrer and a teflon coated thermocouple was added (−)-2,3-dibenzoyl-L-tartaric acid (1000 g, 2.79 mol) followed by acetic anhydride (2 L). The suspension was stirred and heated to 85° C. for 2 h during which time the starting material gradually dissolved. A short time thereafter, the product began to crystallize in the reaction mixture and the suspension was then cooled to 25° C. The product was collected by filtration, washed with 10% acetone in hexane (2×1 L), and dried in a vacuum oven at 50° C. overnight to afford the title compound (22) as a white solid. $^1H$ NMR ($CDCl_3$, 400 MHz): δ 6.0 (s, 2H), 7.45 (app. t, 4H), 7.65 (app. t, 2H), 8.05 (d, 4H).

Step B: 1-Hydroxy-(3R,4R)-2,5-Dioxo-3,4-dibenzoyloxy-pyrrolidine (23)

To a 3-neck 5 L round bottom flask fitted with a mechanical stirrer and a teflon coated temperature probe was added (22) (2.79 mol) followed by acetonitrile (2 L). The suspension was cooled in an ice bath to 4° C., followed by the addition of 50% aqueous hydroxylamine (180 mL, 2.93 mol) over 1 h. The starting material gradually dissolved during the addition and the reaction mixture was warmed to 20° C. and stirred for 1 h. The reaction mixture was concentrated in vacuo, diluted with EtOAc (1 L) and washed with 1 N HCl (2×1 L). The organic phase was separated and concentrated in vacuo to afford a viscous red syrup. The syrup was then heated for two hours in toluene (2.5 L) at 100° C. with azeotropic removal of water. The syrup gradually dissolved and then the product crystallized. After cooling to room temperature the solid was collected by filtration, washed with 10% acetone in hexane (2×1 L) and dried in a vacuum oven to afford the title compound (23) (862 g, 2.43 mol, 87%) as a white solid. $^1H$ NMR ($CDCl_3$, 400 MHz): δ 5.85 (s, 2H), 7.45 (app. t, 4H), 7.65 (app t, 2H), 8.05 (m, 4H).

Step C: (1S)-1-[((3R,4R)-2,5-Dioxo-3,4-dibenzoyloxypyrrolidinyl)-oxycarbonyloxy]-2-methylpropyl 2-methylpropanoate (21)

A 3 L three necked round bottom flask fitted with a mechanical stirrer, teflon temperature probe and an addition funnel was charged with (13) (234 g, 1 mol), (23) (330 g, 0.95 mol), and 1,2-dichloroethane (2200 mL). The reaction mixture was cooled under a nitrogen atmosphere in an ice water bath to 15° C. To the stirred reaction mixture was added a 39% solution of peracetic acid in dilute acetic acid (500 mL, 2.94 mol) over 2 h, while maintaining the temperature between 15 and 22° C. This temperature was maintained for an additional 12 h during which time a white precipitate was formed. The reaction mixture was further cooled to 3-4° C., the product collected by filtration, and washed with hexane (2×1 L). The product was dried in vacuo, yielding the title compound (21) (128 g, 0.24 mol, 25%). The diastereomeric purity of the product was determined to be >99% d.e. by HPLC using a chiral column. $^1$H NMR (CDCl$_3$, 400 MHz): δ 1.0 (d, 6H), 1.2 (dd, 6H), 2.1 (m, 1H), 2.65 (m, 1H), 6.0 (br. s, 2H), 6.6 (d, 1H), 7.45 (app. t, 4H), 7.65 (app. t, 2H), 8.05 (d, 4H).

In an alternative synthesis of compound (21), a 5 L three necked round bottom flask fitted with a mechanical stirrer, teflon coated temperature probe and an addition funnel was charged with (13) (350 g, 1.5 mol), (23) (530 g, 1.5 mol), and dichloromethane (2 L). The reaction mixture was cooled under a nitrogen atmosphere in an ice water bath to 15° C. To the stirred reaction mixture was added a 32% solution of peracetic acid in dilute acetic acid (914 mL, 4.35 mol) over 4 h, while maintaining the temperature between 15° C. and 20° C. The solution was maintained at this temperature for an additional 16 h, then was transferred to a 22 L separatory funnel and the small aqueous layer was removed. The organic phase was diluted with ethyl acetate (2 L) and was washed with water (6×1 L), 0.2M aqueous sodium metabisulfite (2×1 L), and saturated aqueous sodium chloride (2×1 L). The organic phase was dried over anhydrous sodium sulfate and concentrated in vacuo to afford a white solid. This solid was dissolved in ethyl acetate (2 L) at 50° C. and the solution cooled to ambient temperature over 2 h, then further cooled to 0-2° C. for 1 h. The resulting crystalline material was collected on a sintered glass funnel, washed with cold ethyl acetate and dried under vacuum to afford the title compound (21) as a white solid (103 g, 190 mmol, 12.7%), m.p. 138.5-139.5° C. The diastereomeric purity of the product was determined to be 89% d.e. by HPLC using a chiral column.

5.18 Example 18 Synthesis of 4-{[(1S)-Isobutanoyloxyisobutoxy]carbonylamino}-(3R)-(4-chlorophenyl)-butanoic Acid (24)

To a 3 L three necked round bottom flask fitted with a mechanical stirrer, temperature probe, and nitrogen inlet was added (21) (75 g, 139 mmol), R-baclofen (31.2 g, 146 mmol), THF (1000 mL), and water (100 mL). The suspension was stirred under a nitrogen atmosphere at 18-20° C. for 4 h. The reaction became homogenous in 30 min. The solvent was removed in vacuo and the reaction mixture was diluted with methyl tert-butyl ether (250 mL) and washed with 1N HCl (1×500 mL) and water (2×200 mL). The organic phase was separated and concentrated in vacuo to leave a white solid. The solid was purified by flash chromatography (800 g silica gel; eluting with 20% acetone in hexane) to afford the product (50 g, 125 mmol, 90% yield) as a white solid. Crystallization from either an acetone/hexane mixture or ethyl acetate/heptane mixture afforded the title compound (24) (50 g, 125 mmol, 90% yield) as a white solid. The diastereomeric purity of the product was determined to be >99% d.e. by HPLC using a chiral column. $^1$H NMR (CDCl$_3$, 400 MHz): δ 0.89 (m, 6H), 1.15 (m, 6H), 1.94 (m, 1H), 2.52 (m, 1H), 2.58 (dd, 1H), 2.78 (dd, 1H), 3.28 (m, 2H), 3.49 (m, 1H), 4.68 (t, 1H), 6.48 (d, 1H), 7.10 (d, 2H), 7.24 (d, 2H). MS (ESI) m/z 398.14 (M−H)$^-$.

In an alternative synthesis of compound (24), to a 1 L round bottom flask fitted with a mechanical stirrer was added R-baclofen (40.3 g, 189 mmol), compound (21) (99.3 g, 184 mmol, d.e.=89%), acetone (225 mL), methyl tert-butyl ether (525 mL), and water (75 mL). The suspension was stirred at 20-22° C. for 2.5 h. Analysis of the reaction mixture by LC/MS after 1.5 h indicated that starting material (21) had been completely consumed. The reaction mixture was washed with 2% aqueous HCl (30 mL) and saturated aqueous sodium chloride solution (3×200 mL). The organic phase was dried over anhydrous sodium sulfate, filtered, and concentrated in vacuo to provide an orange oil (160 g). The oil was dissolved in dichloromethane (120 mL), and applied to an 800 g Biotage 75 L silica gel chromatography cartridge in a Biotage Flash 75 Radial Compression Module. The dichloromethane was removed by applying a vacuum to the base of the column for 20 minutes. The desired product was eluted from the column with 14% v/v acetone in hexane (20 L total volume). The eluant was initially collected in 500 mL fractions until the product was observed eluting by TLC, at which point it was collected in 2×4 L fractions, then collected in 400 mL fractions until by-product (23) was observed in the eluant (by TLC). The fractions containing no visible impurities by TLC were combined, concentrated under reduced pressure and dried in vacuo to afford the title compound (24) (70 g, 175 mmol, 95% yield). The chemical purity of the product was determined to be ~98.2% AUC (by LC-UV) and the diastereomeric purity determined to be ~88.4% d.e. by HPLC using a chiral column. The product was recrystallized by dissolution of the solid in acetone (175 mL) with warming to 53° C. in a water bath, followed by the gradual addition of hexane (1575 mL) over 45 minutes, maintaining the internal temperature between 47 and 52° C. The clear solution was allowed to cool to ambient temperature over 2 h, followed by further cooling to 0-2° C. for 1 h. The product was collected by filtration and washed with cold acetone/hexane (25 mL/225 mL) and dried in a vacuum oven at 45° C. for 24 h, to give the title compound (24) (59.5 g, 149 mmol) as a white crystalline solid. The chemical purity of the product was determined to be ~99.9% AUC (by LC-UV) and the diastereomeric purity determined to be ~98.7% d.e. by HPLC using a chiral column.

5.19 Example 19 Synthesis of Sodium 4-{[(1S)-Isobutanoyloxyisobutoxy]carbonylamino}-(3R)-(4-chlorophenyl)-butanoate (25)

The carboxylic acid (24) was converted to the sodium salt by dissolution in MeCN and then addition of aqueous NaHCO$_3$ (1 eq.) with sonication for 15 min. The solvent was removed by lyophilization. Crystallization from either mixtures of acetone/hexane, ethyl acetate/heptane, THF/heptane or 1,2-dimethoxyethane/hexane afforded the title compound (25) as a white crystalline solid. 1H NMR (CD$_3$OD, 400 MHz): δ 0.90 (d, 6H), 1.14 (d, 3H), 1.15 (d, 3H), 1.91 (m, 1H), 2.40 (m, 1H), 2.52 (m, 2H), 3.30 (m, 3H), 6.41 (d, 1H), 7.22 (s, 4H). MS (ESI) m/z 398.08 (M−Na)$^-$.

5.20 Example 20 Synthesis of (1R)-1-[((3R,4R)-2 5-Dioxo-3,4-diisobutyroyloxypyrrolidinyl)-oxycarbonyloxy]-2-methylpropyl 2-methylpropanoate (26)

Step A: (3R,4R)-2,5-Dioxo-3,4-diisobutyroyloxy-3,4-dihydrofuran (27)

To a suspension of L-tartaric acid (5.0 g, 33.3 mmol) in toluene (60 mL) was added isobutyryl chloride (11.3 mL, 107 mmol). The resulting suspension was heated to reflux and stirred for 22 h at reflux temperature. The reaction mixture was then concentrated in vacuo to afford a crystalline solid, which was suspended in a mixture of ether and hexane (1:3), filtered, washed with hexane and dried to afford the desired compound (27) as a white crystalline solid (6.4 g, 71%).

¹H-NMR (400 MHz, CDCl₃): δ 1.25 (d, J=6.8 Hz, 12H), 2.72 (hept, J=6.8 Hz, 2H), 5.63 (s, 2H).

Step B: 1-Hydroxy-(3R,4R)-2,5-Dioxo-3,4-diisobutyroyloxypyrrolidine (28)

To a stirred solution of compound (27) (5.98 g, 22 mmol) in ethyl acetate (50 mL) at 0° C. was added a 50% aqueous solution of hydroxylamine (1.75 g, 26.4 mmol). The resulting mixture was stirred at room temperature for 3 h and washed successively with aqueous citric acid solution and brine, then dried over anhydrous sodium sulfate. After filtration and concentration in vacuo, the residue was suspended in toluene and the reaction mixture heated under reflux for 5 h, with the azeotropically liberated water being collected in a Dean-Stark apparatus. Toluene was removed in vacuo to afford the title compound (28) (6.3 g, quantitative yield). ¹H-NMR (400 MHz, CDCl₃): δ 1.22 (d, J 6.8 Hz, 12H), 2.69 (hept, J=6.8 Hz, 2H), 5.48 (s, 2H).

Step C: (1R)-1-[((3R,4R)-2,5-Dioxo-3,4-diisobutryoyloxypyrrolidinyl)-oxycarbonyloxy]-2-methylpropyl 2-methylpropanoate (26)

To a stirred solution of compound (28) (4.89 g, 17.0 mmol) and thiocarbonate (13) (4.39 g, 18.7 mmol) in CH₂Cl₂ at 0° C. was added dropwise a 32% solution of peracetic acid in acetic acid (10.7 mL, 51.1 mmol). The resulting reaction mixture was stirred at 0° C. to r.t. for 21 h, with the reaction progress monitored by NMR. The reaction mixture was washed with water and brine, then dried over anhydrous sodium sulfate. After removal of the solvent in vacuo, the crude product was filtered through a short silica gel column, eluting with 20% ethyl acetate in hexane to afford the desired compound as a mixture of diastereomers. The mixture was carefully crystallized from 5% ether in hexane to afford the title compound (26) (320 mg). The diastereomeric purity of the product was determined to be 82% d.e. by HPLC using a chiral column. ¹H-NMR (CDCl₃, 400 MHz): δ 1.03 (d, J=6.8 Hz, 6H), 1.19 (d, J=6.8 Hz, 6H), 1.22 (d, J=6.8 Hz, 12H), 2.15 (m, 1H), 2.61 (hept, J=6.8 Hz, 1H), 2.69 (hept, J=6.8 Hz, 2H), 5.61 (br.s, 2H), 6.59 (d, J=5.2 Hz, 1H).

5.21 Example 21 Synthesis of 4-{[(1R)-Isobutanoyloxyisobutoxy]carbonylamino}-(3R)-(4-chlorophenyl)-butanoic acid (19)

A suspension of compound (26) and R-baclofen in 10% v/v water-acetonitrile was stirred at room temperature for 4 h. Acetonitrile was removed in vacuo to afford the crude product, which was partitioned between water and ethyl acetate. The organic layer was washed with water (3×) and brine, then dried over anhydrous sodium sulfate. After removal of the solvent in vacuo, the product was crystallized from 20% ethyl acetate -hexane to afford the title compound (19). The diastereomeric purity of the product was determined to be ~92% d.e. by HPLC using a chiral column.

5.22 Example 22 Synthesis of (1S)-1-[((3S,4S)-2,5-Dioxo-3,4-diisobutyroyloxypyrrolidinyl)-oxycarbonyloxy]-2-methylpropyl 2-methylpropanoate (29)

Step A: (3S,4S)-2,5-Dioxo-3,4-diisobutyroyloxy-3,4-dihydrofuran (30)

To a suspension of D-tartaric acid (5.0 g, 33.3 mmol) in toluene (60 mL) was added isobutyryl chloride (11.3 mL, 107 mmol). The resulting suspension was heated to reflux and stirred for 22 h at reflux temperature. The reaction mixture was then concentrated in vacuo to afford a crystalline solid, which was suspended in a mixture of ether and hexane (1:3), filtered, washed with hexane and dried to afford the desired compound (30) as a white crystalline solid (6.4 g, 71%). ¹H-NMR (400 MHz, CDCl₃): δ 1.25 (d, J=6.8 Hz, 12H), 2.72 (hept, J=6.8 Hz, 2H), 5.63 (s, 2H).

Step B: 1-Hydroxy-(3S,4S)-2,5-Dioxo-3,4-diisobutyroyloxypyrrolidine (31)

To a stirred solution of compound (30) (5.98 g, 22 mmol) in ethyl acetate (50 mL) at 0° C. was added a 50% aqueous solution of hydroxylamine (1.75 g, 26.4 mmol). The resulting mixture was stirred at room temperature for 3 h and washed successively with aqueous citric acid solution and brine, then dried over anhydrous sodium sulfate. After filtration and concentration in vacuo, the residue was suspended in toluene and the reaction mixture heated under reflux for 5 h, with the azeotropically liberated water being collected in a Dean-Stark apparatus. Toluene was removed in vacuo to afford the title compound (28) (6.3 g, quantitative yield). ¹H-NMR (400 MHz, CDCl₃): δ 1.22 (d, J=6.8 Hz, 12H), 2.69 (hept, J=6.8 Hz, 2H), 5.48 (s, 2H).

Step C: (1S)-1-[((3S,4S)-2,5-Dioxo-3,4-diisobutryoyloxypyrrolidinyl)-oxycarbonyloxy]-2-methylpropyl 2-methylpropanoate (29)

To a stirred solution of compound (31) (4.89 g, 17.0 mmol) and thiocarbonate (13) (4.39 g, 18.7 mmol) in CH₂Cl₂ at 0° C. was added dropwise a 32% solution of peracetic acid in acetic acid (10.74 mL, 51.06 mmol). The resulting reaction mixture was stirred at 0° C. to r.t. for 21 h, monitoring the reaction progress by NMR. The reaction mixture was washed with water and brine, then dried over anhydrous sodium sulfate. After removal of the solvent in vacuo, the crude product was filtered through a short silica gel column, eluting with 20% ethyl acetate in hexane to afford the desired compound as a mixture of diastereomers. The mixture was carefully crystallized from 5% ether in hexane to afford the title compound (29). The diastereomeric purity of the product was determined to be ~84% d.e. by HPLC using a chiral column. An additional recrystallization affords a product having greater diastereomeric purity. ¹H-NMR (400 MHz, CDCl₃): δ 1.04 (d, J=6.8 Hz, 6H), 1.20 (d, J=6.8 Hz, 6H), 1.24 (d, J=6.8 Hz, 6H), 1.26 (d, J=6.8 Hz, 6H), 2.17 (m, 1H), 2.62 (hept, J=6.8 Hz, 1H), 2.70 (hept, J=6.8 Hz, 2H), 5.63 (br.s, 2H), 6.60 (d, J=5.2 Hz, 1H).

5.23 Example 23 Synthesis of 4-{[(1S)-Isobutanoyloxyisobutoxy]carbonylamino}-(3R)-(4-chlorophenyl)-butanoic Acid (24)

The title compound can also be prepared following the same procedure as in Example 21 by replacing compound (26) with (1 S)-1-[((3 S,4S)-2,5-dioxo-3,4-diisobutryoyloxypyrrolidinyl)-oxycarbonyloxy]-2-methyl propyl 2-methylpropanoate, (29).

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All publications and patents cited herein are incorporated herein by reference in their entirety.

The invention claimed is:

1. A method of synthesizing a 1-(acyloxy)-alkyl N-hydroxysuccinimidyl carbonate compound of Formula (I):

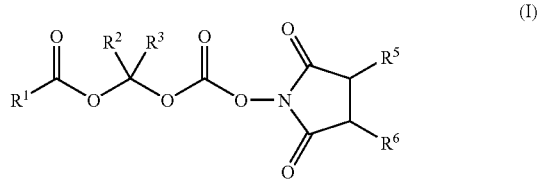

comprising contacting a thiocarbonate compound of Formula (VIII) with an oxidant (IX), in the presence of an N-hydroxysuccinimide compound of Formula (X) to afford the compound of Formula (I);

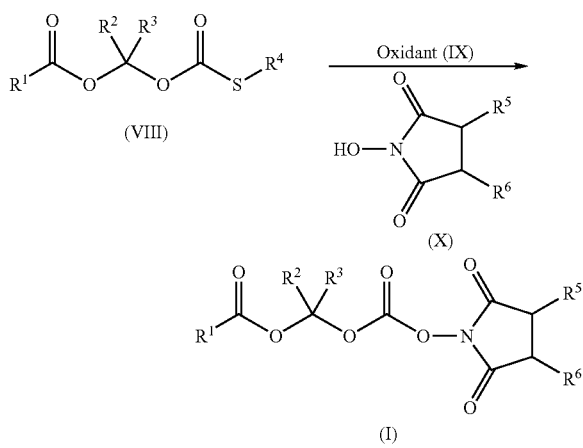

wherein:
- $R^1$ is alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;
- $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl or substituted heteroarylalkyl, or optionally, $R^2$ and $R^3$ together with the atom to which they are bonded form a cycloalkyl, substituted cycloalkyl, cycloheteroalkyl or substituted cycloheteroalkyl ring;
- $R^4$ is $C_{1-4}$ alkyl, phenyl, substituted phenyl or $C_{7-9}$ phenylalkyl; and
- $R^5$ and $R^6$ are independently hydrogen, acylamino, acyloxy, alkoxycarbonylamino, alkoxycarbonyloxy, alkyl, substituted alkyl, alkoxy, substituted alkoxy, aryl, substituted aryl, arylalkyl, carbamoyloxy, dialkylamino, heteroaryl, hydroxy, sulfonamido, or optionally, $R^5$ and $R^6$ together with the atoms to which they are attached form a substituted cycloalkyl, substituted cycloheteroalkyl, or substituted aryl ring.

2. The method of claim 1, wherein $R^1$ is selected from the group consisting of $C_{1-6}$ alkyl, substituted $C_{1-6}$ alkyl, $C_{3-6}$ cycloalkyl, phenyl, substituted phenyl and $C_{7-9}$ phenylalkyl.

3. The method of claim 2, wherein $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl or cyclohexyl.

4. The method of claim 1, wherein $R^2$ and $R^3$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl and $C_{7-9}$ phenylalkyl.

5. The method of claim 4, wherein $R^2$ is hydrogen, methyl, ethyl, n-propyl, isopropyl, n-butyl, isobutyl, sec-butyl, phenyl, cyclohexyl, methoxycarbonyl, ethoxycarbonyl, isopropoxycarbonyl or cyclohexyloxycarbonyl and $R^3$ is hydrogen or methyl, or $R^2$ and $R^3$ together with the carbon atom to which they are attached form a cyclobutyl, cyclopentyl or cyclohexyl ring.

6. The method of claim 1, wherein $R^4$ is methyl, ethyl, propyl, isopropyl, butyl, isobutyl, sec-butyl, tert-butyl, phenyl, 4-methoxyphenyl, 4-methylphenyl or benzyl.

7. The method of claim 1, wherein $R^5$ and $R^6$ are each hydrogen, acyloxy, alkoxycarbonyloxy, alkoxy, carbamoyloxy, hydroxyl, acetoxy, isobutyroyloxy, pivaloyloxy, benzoyloxy, $C_{1-4}$ alkyl-substituted benzoyloxy, methoxy, or benzyloxy.

8. The method of claim 1, wherein $R^1$ is isopropyl, $R^2$ is methyl or isopropyl, $R^3$ is hydrogen, $R^4$ is methyl, ethyl or tert-butyl, and $R^5$ and $R^6$ are each hydrogen, benzoyloxy, isobutyroyloxy, pivaloyloxy or $C_{1-4}$ alkyl-substituted benzoyloxy.

9. The method of claim 1, wherein $R^2$ and $R^3$ in the compound of Formula (I) are different, such that the carbon atom to which $R^2$ and $R^3$ are attached is a stereogenic center.

10. The method of claim 9, wherein the compound of Formula (X) is chiral and non-racemic.

11. The method of claim 10, wherein $R^5$ and $R^6$ in the compound of Formula Formula (X) are each isobutyryloxy or benzoyloxy, and the stereochemistry of the compound is either (1) the stereochemistry at the carbon to which $R^5$ is attached is of the R-configuration, and the stereochemistry at the carbon to which $R^6$ is attached is of the R-configuration; and (2) the stereochemistry at the carbon to which $R^5$ is attached is of the S-configuration, and the stereochemistry at the carbon to which $R^6$ is attached is of the S-configuration.

12. The method of claim 10, wherein the compound of Formula (I) comprises substantially one diastereomer.

13. The method of claim 12, wherein $R^1$ is isopropyl, $R^2$ is isopropyl, $R^3$ is hydrogen, $R^4$ is methyl, ethyl or tert-butyl, $R^5$ and $R^6$ are each benzoyloxy or isobutyroyloxy, and the stereochemistry of the compound is selected from:
  (i) the stereochemistry at the carbon to which $R^2$ and $R^3$ are attached is of the S-configuration, the stereochemistry at the carbon to which $R^5$ is attached is of the R-configuration, and the stereochemistry at the carbon to which $R^6$ is attached is of the R-configuration;
  (ii) the stereochemistry at the carbon to which $R^2$ and $R^3$ are attached is of the R-configuration, the stereochemistry at the carbon to which $R^5$ is attached is of the S-configuration, and the stereochemistry at the carbon to which $R^6$ is attached is of the S-configuration;
  (iii) the stereochemistry at the carbon to which $R^2$ and $R^3$ are attached is of the R-configuration, the stereochemistry at the carbon to which $R^5$ is attached is of the R-configuration, and the stereochemistry at the carbon to which R⁶ is attached is of the R-configuration; and (iv) the stereochemistry at the carbon to which R² and R³ are attached is of the S-configuration, the stereochemistry at the carbon to which R⁵ is attached is of the S-configuration, and the stereochemistry at the carbon to which R⁶ is attached is of the S-configuration.

14. The method of claim 1, wherein said contacting is carried out in the presence of a base.

15. The method of claim 1, wherein the oxidant (IX) comprises a composition selected from the group consisting of a peroxy acid, a peroxide, ozone and oxygen.

16. The method of claim 15, wherein the peroxy acid is selected from the group consisting of peroxyacetic acid, m-chloroperoxybenzoic acid, monoperoxy-o-phthalic acid, monoperoxymaleic acid, peroxytrifluoroacetic acid and salts thereof.

17. The method of claim 1, wherein said contacting is carried out in the presence of a solvent selected from the group consisting of acetic acid, dichloromethane, dichloroethane, chloroform, ethyl acetate, toluene, chlorobenzene, xylene, acetonitrile, methyl tert-butyl ether, cyclohexane or combinations thereof.

18. The method of claim 17, wherein said contacting is carried out at a temperature between about −20° C. and about 80° C.

19. The method of claim 1, wherein said contacting is carried out in the absence of a base.

20. A compound of Formula (I),

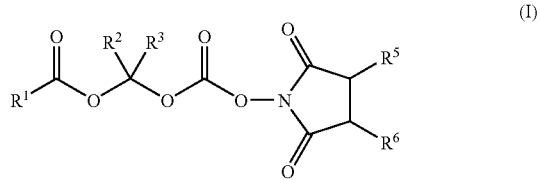

and salts thereof, wherein:
R¹ is phenyl, substituted phenyl, or styryl;
R² is methyl or isopropyl;
R³ hydrogen; and
R⁵ and R⁶ are each hydrogen, benzoyloxy or isobutyroyloxy.

21. The method of claim 1, further comprising:
contacting the compound of Formula (I) with a primary or secondary amine-containing drug of Formula (II) to afford a compound of Formula (III) or a pharmaceutically acceptable salt, or hydrate thereof;

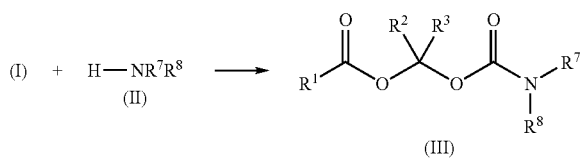

wherein:
HNR⁷R⁸ is a primary or secondary amine-containing drug.

22. The method of claim 21, wherein HNR⁷R⁸ is gabapentin.

23. The method of claim 21, wherein said contacting of the compound of Formula (I) with the primary or secondary amine-containing drug of Formula (II) is conducted in the presence of a solvent selected from the group consisting of acetone, acetonitrile, dichloromethane, toluene, tetrahydrofuran, pyridine, methyl tert-butyl ether, methanol, ethanol, isopropanol, water, and combinations thereof.

24. The method of claim 21, wherein said contacting of the compound of Formula (I) with the primary or secondary amine-containing drug of Formula (II) is carried out at a temperature between about −20° C. and about 40° C.

25. The method of claim 21, wherein said contacting of the compound of Formula (I) with the primary or secondary amine-containing drug of Formula (II) is performed in the absence of a base.

26. The method of claim 21, wherein said contacting of the compound of Formula (I) with the primary or secondary amine-containing drug of Formula (II) is performed in the presence of a base.

27. The method of claim 21, wherein the base is an alkali metal bicarbonate, an alkali metal carbonate salt or an organic base selected from the group consisting of triethylamine, diisopropylethylamine, N-methylmorpholine, and pyridine.

28. The method of claim 21, wherein HNR⁷R⁸ is pregabalin.

29. The method of claim 21, wherein HNR⁷R⁸ is tranexamic acid.

30. A method of synthesizing a 1-(acyloxy)-alkyl carbamate prodrug of pregabalin or a salt or hydrate thereof, comprising contacting a compound of Formula (I) with pregabalin or a salt, thereof:

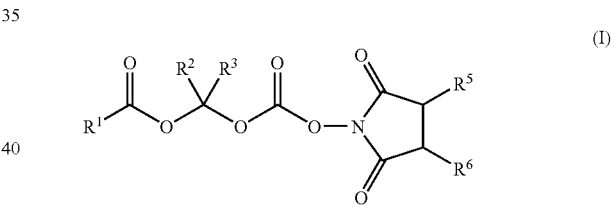

wherein R¹, R², R³, R⁵ and R⁶ are as defined in claim 1.

31. A method of synthesizing a 1-(acyloxy)-alkyl carbamate prodrug of tranexamic acid or a salt or hydrate thereof, comprising contacting a compound of Formula (I) with tranexamic acid or a salt thereof:

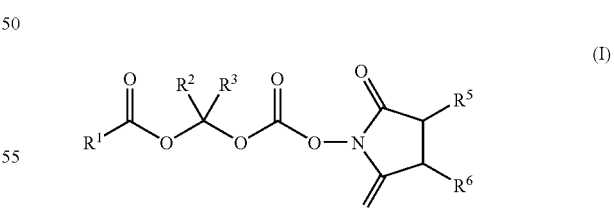

wherein R¹, R², R³, R⁵ and R⁶ are as defined in claim 1.

32. The method of claim 21, wherein HNR⁷R⁸ is R-baclofen.

* * * * *